(12) United States Patent
Chalupa et al.

(10) Patent No.: US 7,097,835 B2
(45) Date of Patent: Aug. 29, 2006

(54) IMMUNOSELECTIVE TARGETING AGENTS AND METHODS OF USE THEREOF

(75) Inventors: Leo M Chalupa, Davis, CA (US); Emine Gunhan, Babil Caddesi (TK); Prabhakara V. Choudary, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 462 days.

(21) Appl. No.: 10/198,003

(22) Filed: Jul. 17, 2002

(65) Prior Publication Data

US 2006/0165705 A1 Jul. 27, 2006

Related U.S. Application Data

(60) Provisional application No. 60/306,472, filed on Jul. 18, 2001.

(51) Int. Cl.
*A61K 39/395* (2006.01)
*C07K 21/08* (2006.01)

(52) U.S. Cl. ............... 424/130.1; 424/178.1; 424/179.1; 424/183.1; 424/181.1; 530/388.1

(58) Field of Classification Search ............... 435/7.2, 435/387.1; 436/63; 514/2, 13; 530/320, 530/350, 402; 424/13.1
See application file for complete search history.

(56) References Cited

U.S. PATENT DOCUMENTS 5,744,580 A * 4/1998 Better et al. ............... 530/377

OTHER PUBLICATIONS

De Gois et. al., Biological Chemistry, 275(47):36683-36690, 2000.*
DiStefano et. al., J. Cell. Biol. 101:1107-1114, 1985.*
Fracasso et. al., Mini-reviews in Medicinal Chemistry, 4:545-62, 2004.*
Parsons, FASEB J, 14:2423-2434, 2000.*
Varoqui et. al., Prog Brain Res, 109:83-95, 1996.*
Weihe et. al., PNAS, 93:3547-3552, 1996.*
Wiley et. al., J Neuroscience Methods, 103:73-82, 2000.*
Wiley et. al., Brain Res. 562:149-153, 1991.*
Wenk et. al., Brain Research, 679:8-14, 1995.*
Deen et. al., J Immunol Methods, 129:119-25.*
He and Masland, (1997), *Nature*, 389:378-382.
Johnson and Reese, (2000), 2000 Association for Research in Vision and Ophthalmology, Inc. (ARVO), Annual Meeting in Fort Lauderdale, Apr. 30-May 5, 2000, IOVS Abstract Issue 41(4):#4507, Mar. 8.
Wiley, (1996), *Sem. Cancer Biol.*, 7:71-77.
Wiley et al., (1997), *Neurosci. Lett.*, 230:97-100.
Youle et al. (1980), *Proc. Natl. Acad. Sci. USA*, 77:5483-5486.
Flavell, (1998), *Curr. Top. Microbiol. Immun.*, 234:57-61.
Carlsson et al., (1978), *Biochem. J.*, 173:723-737.
Robertson et al., (1998), *Cerebral. Cortex*, 8:142-155.
Vaney, (1990), *Prog. in Retinal Res.*, 9:49-100.
Burgi and Grzywacz, (1994), *J. Neuroscience*, 14:7246-7439.
Hu et al., (1998) *Glia*, 24:187-197.
McGurk et al., (1987) *Neuroscience*, 22:215-224.

* cited by examiner

*Primary Examiner*—Eileen B. O'Hara
*Assistant Examiner*—Sandra Wegert
(74) *Attorney, Agent, or Firm*—Paula A. Borden; Carol L. Francis; Bozicevic Field & Francis LLP

(57) ABSTRACT

The present invention provides immunoselective targeting agents that bind to transporters that are transiently accessible on the surface of neuronal cells, and that deliver compounds selectively to such cells. The invention provides methods of selectively killing, as well as methods of selectively promoting survival of, a neuronal cell.

12 Claims, 7 Drawing Sheets

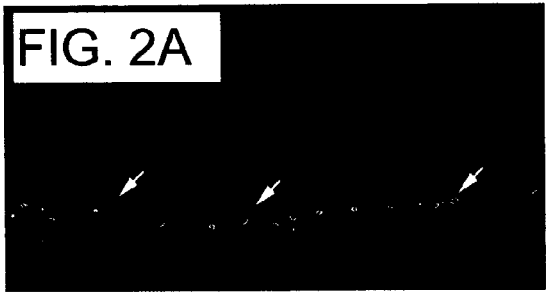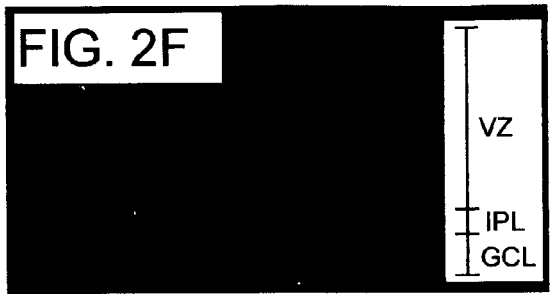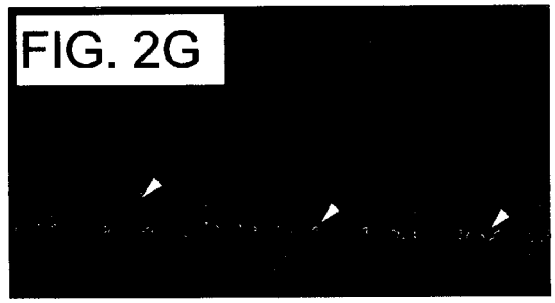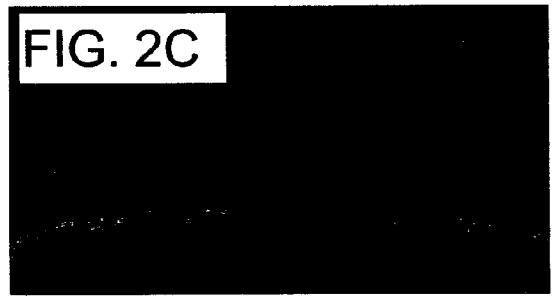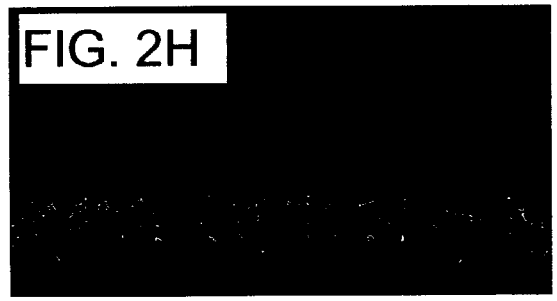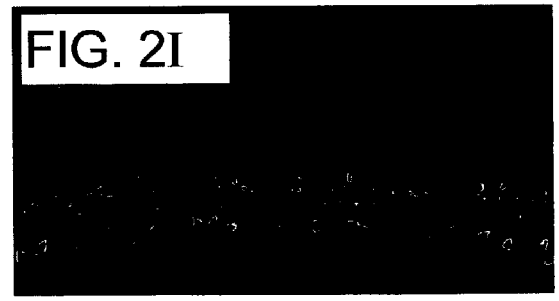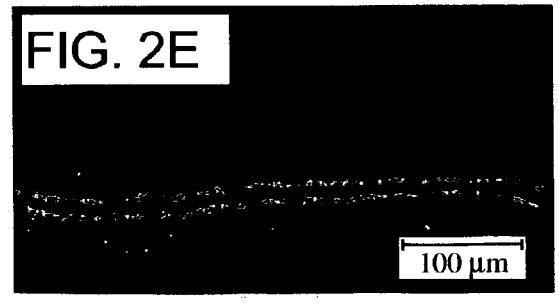

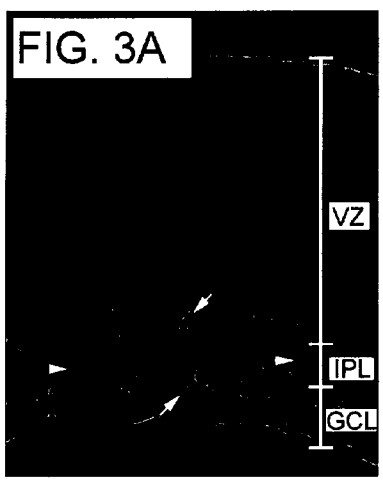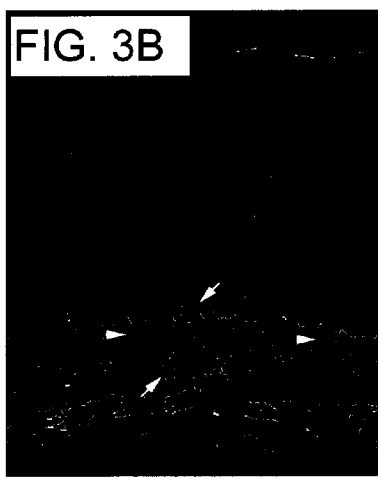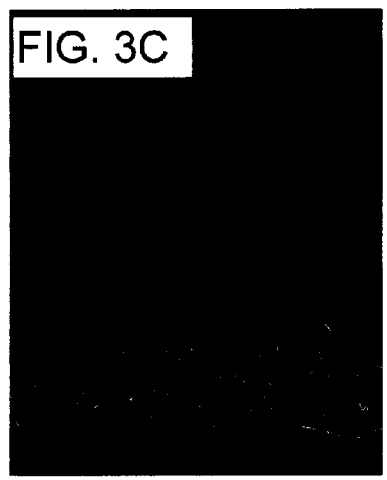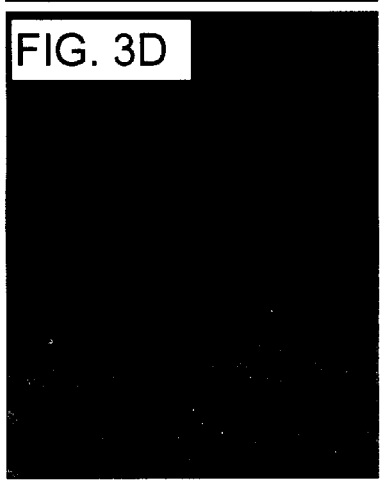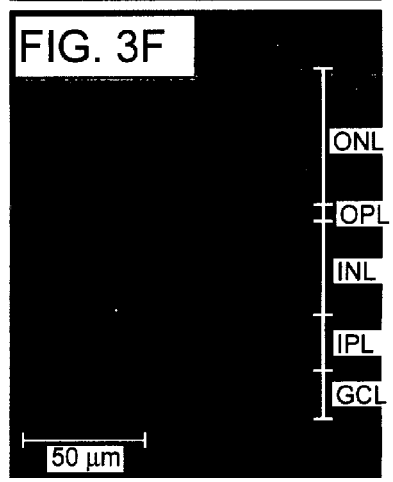

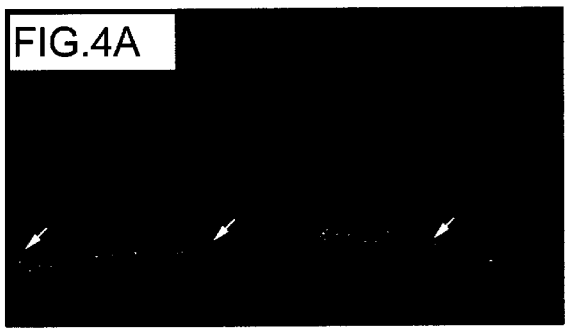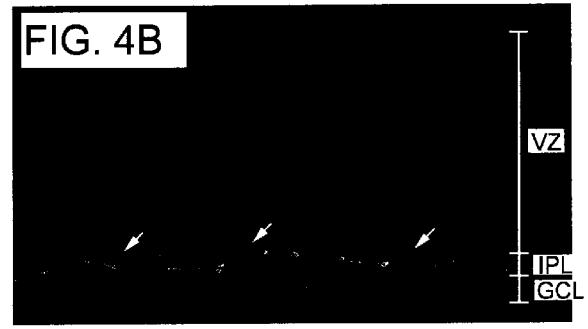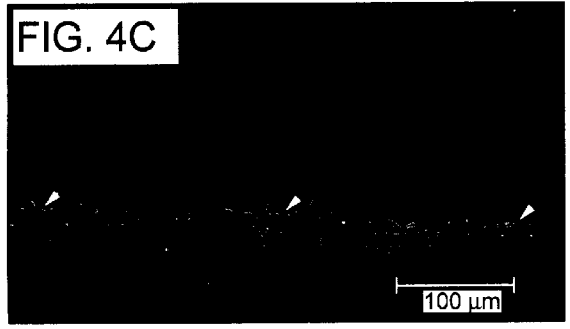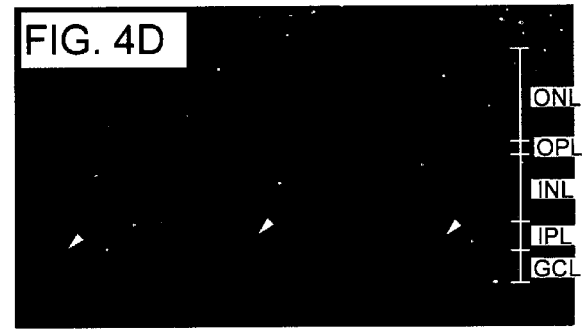

FIG. 6A
FIG. 6B
FIG. 6C
FIG. 6D
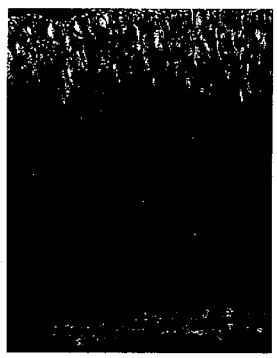
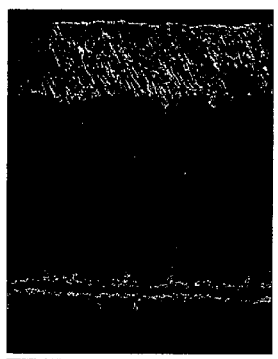
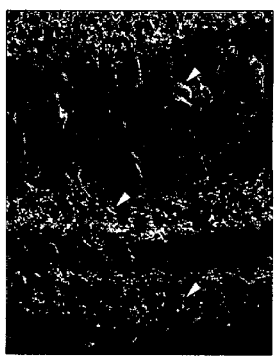
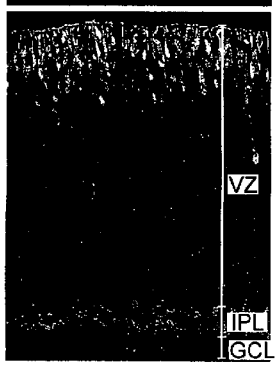
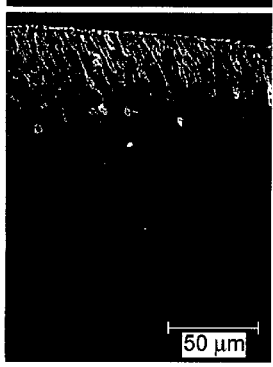
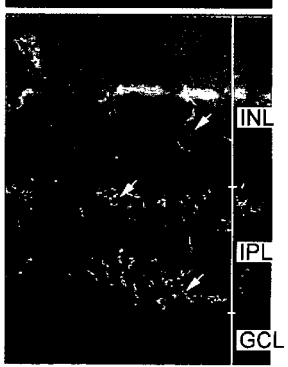

IMMUNOSELECTIVE TARGETING AGENTS AND METHODS OF USE THEREOF

CROSS-REFERENCE

This application claims the benefit of U.S. Provisional Patent Application No. 60/306,472 filed Jul. 18, 2001, which application is incorporated herein by reference in its entirety.

STATEMENT REGARDING FEDERALLY SPONSORED RESEARCH

This invention was made with Government support under grant no. EY03391, awarded by the National Institutes of Health. The government may have certain rights in this invention.

FIELD OF THE INVENTION

The present invention is in the field of selective targeting agents, and selective delivery of an agent to a target neuronal cell.

BACKGROUND OF THE INVENTION

The ability to deplete specific populations of cells provides a powerful tool for the study of the role of particular cells in, for example, development and other biological processes. For example, the ability to selectively deplete neurons provides neurobiologists tools to study the involvement of different cell types in the functional and structural organization of the nervous system. A number of methods have been devised for this purpose in the context of neuronal cell depletion, including photoablation (He and Masland, 1997 Nature 389:378–382), systemic administration of excitatory neurotransmitters (Johnson and Reese, 2000 Association for Research in Vision and Ophthalmology, Inc. (ARVO), Annual Meeting in Fort Lauderdale, Apr. 30–May 5, 2000, IOVS Abstract Issue 41(4):#4507, Mar. 8, 2000), as well as the administration of immunotoxins directed at specific receptors expressed by targeted neurons (Wiley, 1996 Sem Cancer Biol 7:71–77; Wiley et al. 1997 Neurosci Lett 230:97–1000; Youle et al. 1980 Proc. Natl. Acad Sci USA 77:5483–5486; Flavell, 1998 Curr Top Microbiol. Immun 234:57–61). It is also desirable to delete cells at specific stages of development and to localize effects to a confined region of the nervous system. The effectiveness of a given method is evaluated by its selectivity (e.g., killing of the target cell with little or not killing of non-target cells) and by how completely the method succeeds in eliminating a targeted cell population.

Toxins that can be used to kill cells are generally referred to as cytotoxins. Ribosome inactivating proteins (RIPs), which are a class of proteins ubiquitous in higher plants, are examples of such cytotoxins. RIPs, which are divided into Type I and Type II classes, are cytotoxic due to their activity as potent inhibitors of eukaryotic protein synthesis. Type I RIPS are composed of a single peptide chain having ribosome-inactivating activity, while Type II proteins are composed of an A-chain, essentially equivalent to a Type I protein, disulfide-linked to a B-chain having cell-binding properties. The N-glycosidic bond of a specific adenine base is hydrolytically cleaved by RIPs in a highly conserved loop region of the 28S rRNA of eukaryotic ribosomes, thereby inactivating translation in eukaryotic cells. See, e.g., U.S. Pat. No. 5,744,580. Gelonin, dodecandrin, tricosanthin, tricokirin, bryodin, Mirabilis antiviral protein (MAP), barley ribosome-inactivating protein (BRIP), pokeweed antiviral proteins (PAPS), saporins, luffins, and momordins are examples of Type I RIPs; whereas ricin and abrin are examples of Type II RIPS.

One conventional protocol for constructing an immunotoxin to a targeted cell involves three basic steps: (i) activating the targeting antibody using the heterobifunctional cross-linking agent, N-succinimidyl 3-(2-pyridildithio)propionate (SPDP) to generate sulfhydryl-reactive pyridyldisulfide groups; (ii) modifying the cytotoxin (e.g., a RIP, such as saporin), to contain -SH functional groups; and (iii) mixing the modified antibody and saporin molecules together. The result is a cross-linked antibody-toxin conjugate containing "cleavable" bonds (Carlsson et al., 1978 Biochem. J. 173:723–737). One of the most widely used immunotoxins, 192 IgG-saporin, has been directed at cholinergic neurons in basal forebrain (Robertson et al., 1998 Cerebral. Cortex 8:142–155). The 192 IgG-saporin is targeted to the p75 receptor since it is believed that most cholinergic cells in basal forebrain express this low affinity neurotrophin receptor.

Depletion of cholinergic cells have been of particular interest in the examination of developmental and functional pathways. A common cholinergic cell of interest is the amacrine cell. Cholinergic amacrine cells are arguably one of the best characterized of the more than 40 different amacrine cells thought to be present in the mammalian retina (Vaney, 1990 Prog. in Retinal Res. 9:49–100). These retinal interneurons have been suggested to play several key functions during the development of the retina as well as in the functional organization of the mature retina. A developmental phenomenon ascribed to cholinergic amacrine cells is the generation of retinal waves of activity thought to be crucial for the refinement of patterns of projections in the developing visual system (Burgi and Grzywacz, 1994 J. Neuroscience 14:7246–7439). The use of immunotoxins in research would make it feasible to assess the effects of selectively eliminating these retinal interneurons on the generation of activity patterns in the developing and mature retina.

Unfortunately, use of immunotoxins in various applications (e.g., as research reagents) has been frustrated due to the lack of specificity of the immunotoxin (which can result in killing of or damage to non-target cells) and/or the inefficiency of killing of target cells. For example, the effects of cholinergic cell depletion on the formation of functional, developmental, and structural pathways is a frequent subject of research. However, none of the currently available methods permits selective elimination of the entire population of the targeted cell type. The 192 IgG-saporin immunotoxin in present use is no exception, at least in part because the target site of the immunotoxin, the NGF (p75) receptor, is expressed by several other retinal cell types, including some ganglion cells and Muller glial cells (Hu et al., 1998 Glia 24:187–197). Therefore, other non-target cells nearby are also eliminated. In addition, the effectiveness of 192 IgG-saporin in eliminating cholinergic neurons has been reported to be quite variable at other levels of the nervous system, ranging from just over 40% to more than 90% (Robertson et al., 1998 Cerebral Cortex 8:142–155). Furthermore, the toxins currently employed for eliminating cholinergic cells have serious shortcomings that limit their usefulness. For instance, the AF64A toxin has been found to induce non-specific damage both in the retina as well as at other levels of the central nervous system (McGurk et al., 1987 Neuroscience 22:215–224).

There is a need in the field for immunoselective targeting agents that selectively and efficiently deliver compounds to a target population of neuronal cells, either for elimination of such cells or to promote survival of such cells. The present invention addresses this need.

SUMMARY OF THE INVENTION

The present invention provides immunoselective targeting agents that bind to transporter proteins that are transiently accessible on the surface of neuronal cells, and that deliver compounds selectively to such cells. The invention provides methods of selectively killing, as well as methods of selectively promoting survival of, a neuronal cell.

BRIEF DESCRIPTIONS OF THE DRAWINGS

The patent or application file contains at least one drawing executed in color. Copies of this patent or patent application publication with color drawing(s) will be provided by the Office upon request and payment of the necessary fee.

FIGS. 2A–J show vertical sections of developing rat retinas with the corneal side at the bottom showing amacrine cells. The left column (FIGS. 2A–E) is showing the immunochemical marker VAChT, and the right column (FIGS. 2F–J) shows the immunochemical marker ChAT. From top to bottom, the images are from birth (P0, postnatal day 0) to adult (P0, P2, P6, P12, and adult). VZ is the ventricular zone. IPL is the inner plexiform layer. GCL is the ganglion cell layer. ONL is the outer nuclear layer. OPL is the outer plexiform layer. INL is the inner nuclear layer. The arrows show the earliest VAChT staining at P0 (FIG. 2A), while the earliest ChAT staining is at P2 (FIG. 2G).

FIGS. 3A–F are a series of photographs showing retinal cross-sections after injection of the cytotoxin. FIGS. 3A–D are P1 retinas collected 3, 6, 12 and 18 hours after toxin injection. FIG. 3E is a P2 retina 24 h after injection. FIG. 3F is a P6 retina 5 days after injection. The arrows show the toxin concentrated in the IPL and immediately adjacent to the IPL.

FIGS. 4A–D are a series of photographs showing retinal cross sections immunostained for ChAT, in red, against a background of DAPI nuclear stain, in blue. The images in FIGS. 4A and 4B are from rat retinas injected at P1 with vehicle (left) or immunotoxin (right). FIGS. 4C and 4D are retinas from rats sacrificed at P6. The arrows show changes in ChAT immunoreactivity at P2, and the arrowheads show complete loss of cholinergic amacrine cells by P6.

Figure 5A:
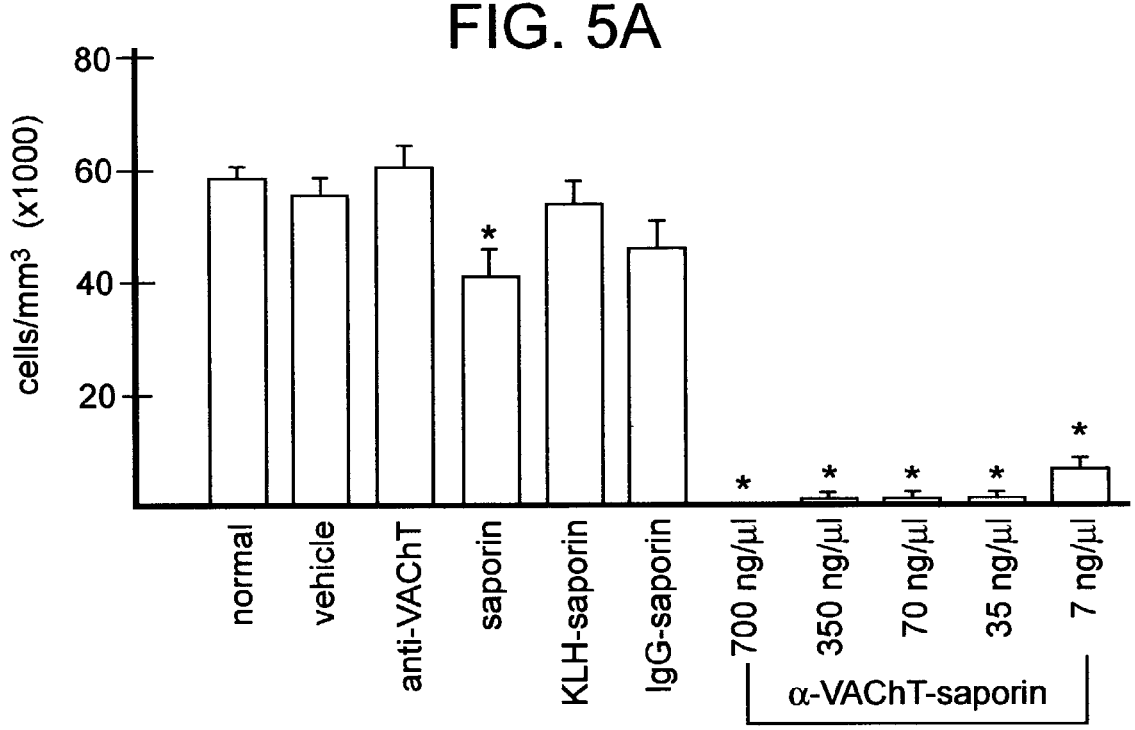
Figure 5B:
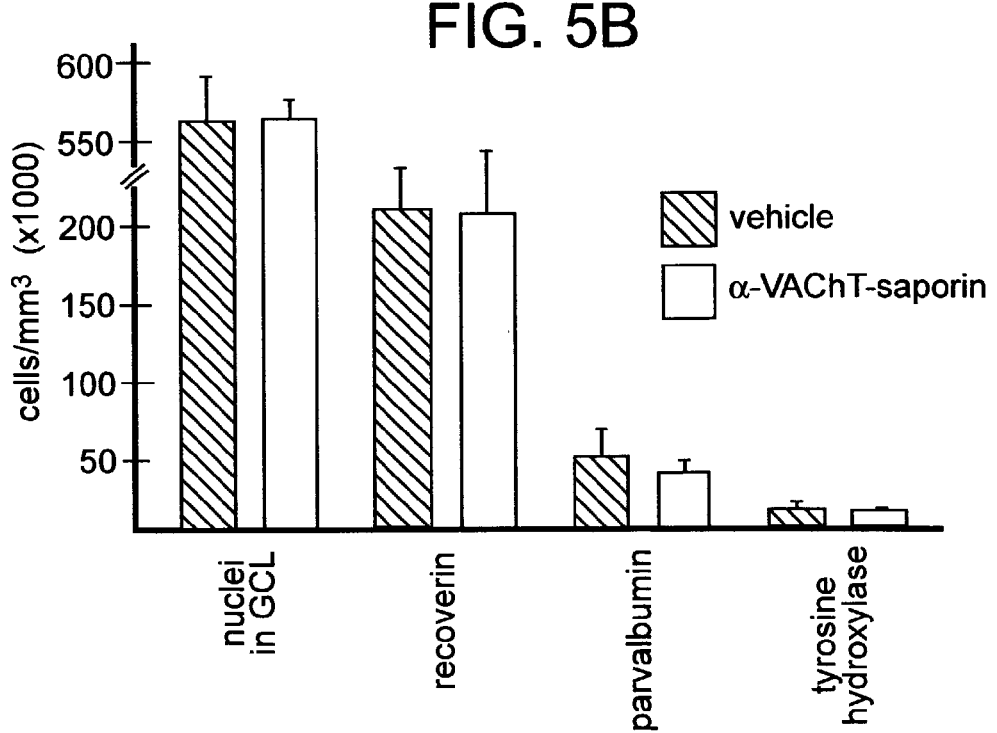

FIG. 5A is a histogram that compares the number of cholinergic amacrine cells labeled with ChAT (per $mm^3$) from a series of controls for immunotoxin structure and function. FIG. 5B is a histogram showing cell counts for other cell types in the inner retina after injection with either vehicle or anti-VAChT-saporin. Values are against mean±SEM.

FIGS. 6A–D are a series of photographs showing rat retinas injected at P1 with vehicle (top panel in each of 6A–D) or toxin (bottom panel in each of 6A–6D) and labeled with anti-recoverin antibody for cone bipolar cells, in green, and anti-VAChT antibody for cholinergic amacrine cells, in red. The rats were sacrificed at P2 (FIG. 6A), P6 (FIG. 6B), P12 (FIG. 6C) and P20 (FIG. 6D). The arrows show cone bipolar cells migrating from the ventricular zone, and the arrowheads show the axons extending to two distinct strata in the IPL.

Figure 7A:
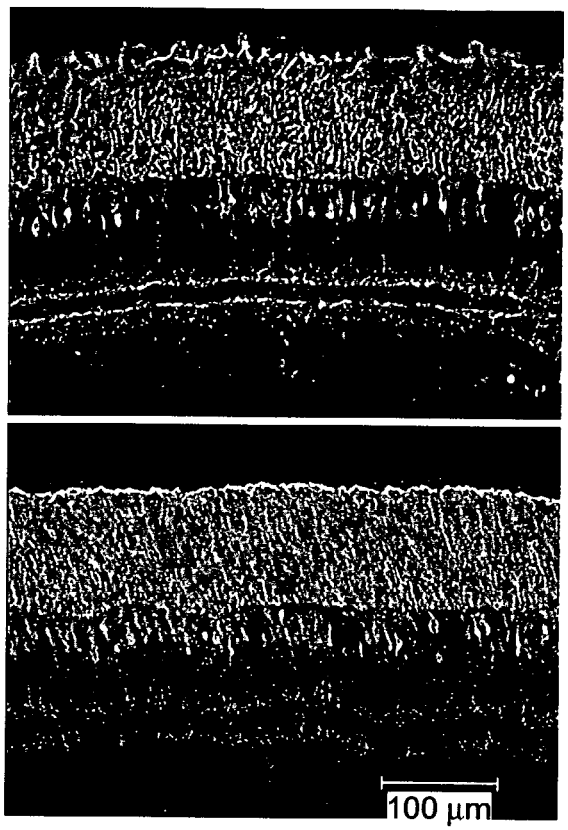
Figure 7B:
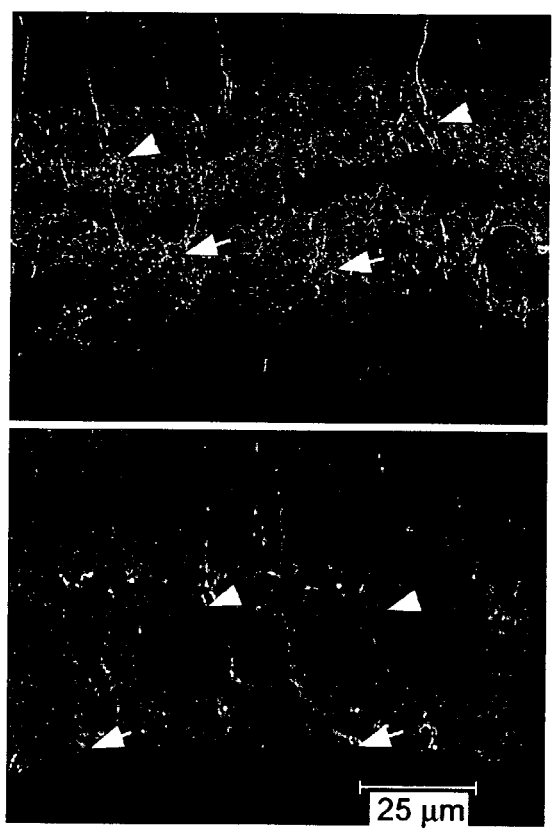

FIGS. 7A and 7B is a series of photographs showing retinal cross-sections double immunostained with anti-recoverin for cone bipolar cells, in green, and anti-VAChT for cholinergic amacrine cells, in red. The top panels of each of FIGS. 7A and 7B is vehicle-injected retinas and the bottom panels of FIGS. 7A and 7B is toxin-injected retinas. The left column shows the general morphology of the retina unaffected by toxin treatment. The right column, at higher magnification, shows the fine structure of cone bipolar cells and axonal targets that are unaffected by the loss of the cholinergic amacrine cells. The arrows show On bipolar terminals in the inner IPL, and the arrowheads show Off bipolar terminals in the outer IPL.

DEFINITIONS

"Biotoxin" as used herein refers to a molecule comprising a receptor binding component and a toxin component. The receptor-binding component generally binds a cell-surface-accessible protein or portion thereof. The receptor-binding component can be a receptor specific for a cell surface ligand, a ligand for a cell surface receptor or an antibody that specifically binds a cell surface antigen.

As used herein, the term "immunoselective targeting agent" refers to an agent comprising an antibody that specifically binds an epitope on a transporter protein (e.g., a vesicular transporter) that is accessible to the surface of a neuronal cell; which antibody is linked to a substance that is cytotoxic to, or promotes the survival of, a neuronal cell. As used herein, the term "immunoselective targeting agent" includes immunotoxins as well as antibody linked to a substance that prolongs survival of a neuronal cell.

"Immunotoxin" or "immunocytotoxin" as used herein refers to a molecule comprising protein having specific antigen binding activity (e.g., an antibody or antibody fragment that specially binds an antigen) that is covalently attached to a toxin that has activity in effecting killing of a target cell (e.g., a eukaryotic cell, particularly a mammalian cell). "Immunotoxin" refers to any cytotoxin conjugated to an immunoglobulin or Fab fragment, directed against a specific antigen.

By "ribosome inactivating protein" (RIP) is meant a protein, preferably a toxin, which is able to disrupt the normal ribosome function of a cell, eventually leading to cell death.

"Saporin" is an example of a RIP, which can be isolated from the seeds of the plant *Saponaria officinalis*.

"VAChT" refers to Vesicular Acetylcholine Transporter, which is present on the surface of vesicles that store acetylcholine (ACh) within cholinergic neurons. VAChT becomes surface-accessible during release of ACh from vesicles to the synaptic cleft.

"EDC" refers to 1-ethyl-3 [3-dimethylaminopropyl]carbodiimide hydrochloride and equivalents thereof used in the covalent attachment of an antibody to a cytotoxin to provide an immunotoxin according to the invention.

"Selective depletion" in the context of the use of an immunotoxin of the invention refers to killing of target cells at levels that are significantly greater than non-target cells, e.g., with little or no detectable killing of non-target cells.

"Complete depletion" refers to depletion of target cells in a population of cells following contact of an immunotoxin of the invention so that no detectable viable, healthy (e.g., undamaged) target cells remain.

By "isolated" in the context of, for example, an isolated protein, is meant that the protein is at least 20%, by weight, free from the proteins and naturally-occurring organic molecules with which it is naturally associated. Preferably, the preparation is at least 75%, more preferably at least 90%, and most preferably at least 99%, by weight, the protein of interest. An isolated protein may be obtained, for example, by extraction from a natural source, by expression of a recombinant nucleic acid encoding a protein of interest, or by chemically synthesizing the protein. Purity can be measured by any appropriate method, e.g., column chromatography, polyacrylamide gel electrophoresis, or HPLC analysis.

The terms "polypeptide" and "protein", used interchangeably herein, refer to a polymeric form of amino acids of any length, which can include coded and non-coded amino acids, chemically or biochemically modified (e.g., post-translational modification such as glycosylation) or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The terms "host," "subject," "individual," and "patient" are used interchangeably herein to refer to an individual amenable to application of the methods of the invention, e.g., diagnostic methods, and treatment methods. Subjects include mammals; birds; reptiles; fish; amphibians; and invertebrates, including insects, nematodes, etc. Mammals include humans, non-human primates, rodents, canines, felines, ungulates, rodents, etc. Mammalian subjects and patients, particularly human subjects or patients are of particular interest in some embodiments.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "antigen" and "epitope" are well understood in the art and refer to the portion of a macromolecule, such as a polypeptide, which is specifically recognized by a component of the immune system, e.g., an antibody. As used herein, the term "antigen" encompasses antigenic epitopes, e.g., fragments of an antigen.

The term "binds specifically," in the context of antibody binding, refers to high avidity and/or high affinity binding of an antibody to a specific polypeptide i.e., an epitope of a transporter polypeptide. Antibody binding to an epitope on a specific transporter polypeptide (also referred to herein as "a transporter epitope", with vesicular transporter epitopes being of particular interest) is preferably stronger than binding of the same antibody to any other epitope, particularly those which may be present in molecules in association with, or in the same sample, as the specific polypeptide of interest, e.g., binds more strongly to a specific transporter epitope than to a different transporter epitope so that by adjusting binding conditions the antibody binds almost exclusively to the specific transporter epitope and not to any other transporter epitope, and not to any other transporter polypeptide which does not comprise the epitope.

Before the present compositions and methods are described, it is to be understood that this invention is not limited to particular compositions and methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an immunoselective targeting agent" includes a plurality of such agents and reference to "the neuronal cell" includes reference to one or more neuronal cells, and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides immunoselective targeting agents that bind to one or more cell surface-accessible epitopes of transporters that are at least transiently accessible on the surface of neuronal cells, and deliver compounds selectively to the cytoplasm of such cells. The immunoselective targeting agents of the invention bind specifically to transporters that are transiently accessible on the surface of neuronal cells. Immunoselective targeting agents that bind a cell surface accessible of a vesicular transporter are of particular interest. The immunoselective targeting agents of the invention are useful for delivering a substance selectively to a neuronal cell. Substances of interest include those that are cytotoxic, and those that promote survival of a cell. Accordingly, the invention provides methods of selectively killing, as well as methods of selectively promoting survival of, a neuronal cell. Methods of selectively killing, or depleting, a neuronal cell are useful in research applications, in creating animal models of diseases, as well as in therapeutic applications. Methods of selectively promoting survival of a neuronal cell are useful in various therapeutic applications.

The present invention is based on the discovery that linkage (e.g., covalent attachment) of an antibody, specific for a transporter (e.g., a vesicular transporter), to a cytotoxin by mixing these entities in the presence of an effective amount of 1-ethyl-3[3-dimethylaminopropyl]carbodiimide hydrochloride (EDC) results in the production of an immunoselective targeting agent (e.g., an immunotoxin) that has improved characteristics of selective killing of target neuronal cells having a transiently surface-accessible transporter to which the antibody portion of the immunoselective targeting agent binds. The invention is further based on the discovery that vesicular transporter molecules are particularly desirable as target antigens to which the antibody portion of the immunoselective targeting agent selectively binds. Vesicular transporter molecules in effect facilitate internalization of the immunoselective targeting agent, thus facilitating delivery of the antibody-linked substance to the target neuronal cell.

The finding that an immunoselective targeting agent that comprises an antibody specific for a vesicular transporter is effective in selectively targeting and delivering agents to a particular neuronal cell population was unexpected, as vesicular transporters are surface-accessible transiently, e.g., during release of a neurotransmitter from a vesicle to the synaptic cleft.

Accordingly the present invention provides immunoselective targeting agents, as well as methods of producing the immunoselective targeting agent, that have the unexpected advantage of providing for selective delivery of a substance to a target neuronal cell. In short, the invention is based upon the covalent attachment of a cytotoxin or a substance that promotes cell survival to an antibody that specifically binds a transiently cell surface accessible transporter on a target neuronal cell.

Immunoselective targeting agents of the invention are useful in various research and therapeutic applications. For example, where a subject immunoselective targeting agent is an immunotoxin (e.g, and antibody specific for a vesicular transporter linked to a cytotoxic substance), a subject immunoselective targeting agent finds use both in research applications (e.g., to study the role of a particular neuronal cell type in development or in a disease state); and in therapeutic applications (e.g., in the destruction of unwanted neuronal cells). Where a subject immunoselective targeting agent comprises a substance that promotes cell survival, a subject immunoselective targeting agent is useful in a variety of therapeutic applications, e.g., for treatment of disorders related to or caused by death of a neuronal cell or neuronal cell population.

Immunoselective Targeting Agents

The present invention provides immunoselective targeting agents that bind to transiently cell surface accessible transporters on the surface of neuronal cells (e.g., vesicular transporters), and deliver compounds selectively to the cytoplasm of such cells. The immunoselective targeting agents of the invention bind specifically to epitope(s) of transporters that are transiently accessible on the surface of neuronal cells. The immunoselective targeting agents of the invention are useful for delivering a substance selectively to a neuronal cell. Substances of interest include those that are cytotoxic, and those that promote survival of a cell.

Target Antigens

Figure 1A:
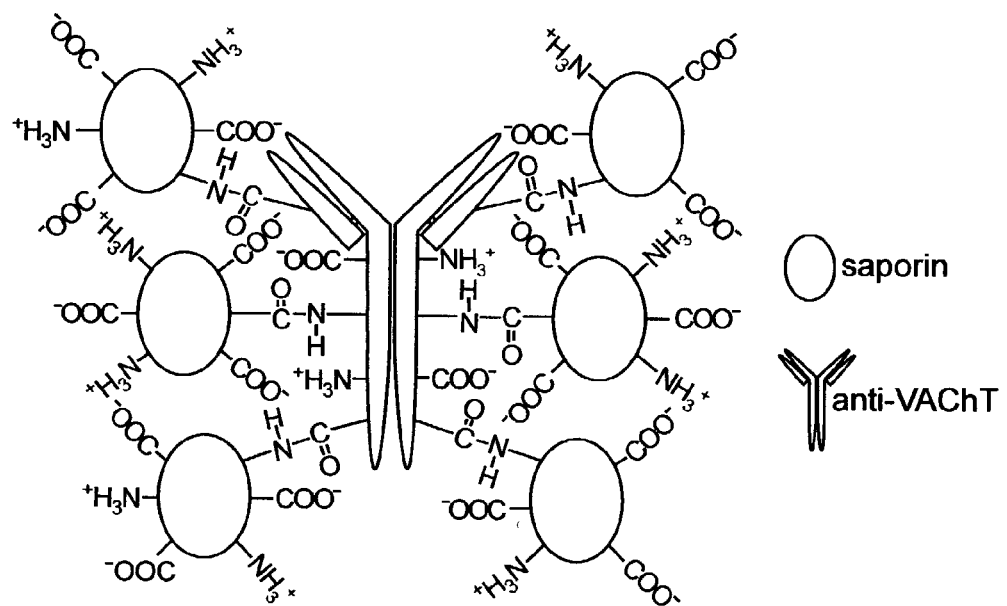
FIG. 1A is a schematic illustration of the structure and cellular mechanism of action of the anti-VAChT-saporin immunotoxin.

The immunoselective targeting agents of the invention bind specifically to transporter polypeptides that are transiently accessible on the surface of neuronal cells. Such transiently cell surface accessible transporters are those which are not consituitively present on the surface of a target cell, e.g., are "recycled" through endocytosis. Vesicular transporters are of particular interest. A "transporter protein" refers to a protein that facilitates movement of one or more molecule(s) from the cytoplasm to the cell surface and/or from the cell surface (as in an extracellular or cell membrane-associated molecule) to the cytoplasm of a neuronal cell. Thus, the transporter protein is exposed at the cell surface for at least part of the course of its mechanism in transport, and thus is at least transiently accessible from the extracytoplasmic cell surface. FIG. 1A illustrates the movement of the exemplary vesicular transporter protein VAChT from its role in facilitating incorporation of acetylcholine in synaptic vesicles, to release at the cell surface, and internalization for recycling of vesicles.

Vesicular transporter proteins of particular interest include, but are not necessarily limited to, vesicular acetylcholine transporter (VAChT); vesicular monoamine transporter (e.g., vesicular monamine transporters 1 and 2 (VMAT1 and VMAT2), e.g., present in monoaminergic neurons, e.g., dopaminergic, serotonergic, and noradrenergic neurons); vesicular glutamate transporter (e.g., VGLUT, VGLUT2, VGLUT3, and differentiation-associated $Na^+$-dependent inorganic phosphate cotransporter (DNPI); vesicular glycine transporter; vesicular GABA transporter (VGAT); vesicular inhibitory amino acid transporter (VI-AAT); and the like.

The amino acid sequences of vesicular transporters from various organisms are known, e.g., the amino acid sequences of the following vesicular transporters are found in the GenBank database: (1) VAChT: GenBank Accession Nos. U10554, NM_057790, AF030197, and U09211; (2) DNPI: AB032435 and NM_053427; VMAT1: L00603 and U39905; VMAT2: NM_013031 and L23205; VGAT: AF030253; VGLUT2: AF324864; VGLUT3: AJ491795 and NM_139319; VIAAT: AY044836, NM_080552, and NM_031782.

Target Cells

The immunoselective targeting agents of the invention can be produced to specifically bind any of a variety of target antigens that are substantially specific for a desired target cell. "Target cell" as used herein refers to a neuronal cell that transiently displays a particular transporter on its surface (e.g., a vesicular transporter), or on which a transporter is transiently surface-accessible. A "non-target cell" is a cell that does not display on its cell surface the particular transporter displayed by a target cell. Thus, an immunoselective targeting agent is selective for a particular neuronal cell, e.g., binding to non-target cells is minimized, avoided, or undetectable.

In some embodiments, of particular interest are cells of an animal model, where a subject immunoselective targeting agent comprises a cytotoxic moiety, and the immunoselective targeting agent is a reagent to study the effects of target cell depletion. The target cell may be present in its natural milieu (e.g., the cell is an in vivo cell), or may be isolated (e.g., as a section of tissue or in culture). The target cell may also be a primary or immortalized cell line (e.g., such as those available from the ATCC). In other embodiments, a target cell is an in vivo cell of an individual.

In some embodiments, e.g., where the transporter is VAChT, the target cell is a cholinergic cell. Cholinergic cells include, but are not limited to, cholinergic amacrine cells in the retina, cholinergic cells in the basal forebrain, striatum, amygdala, hippocampus, motor nucleus for facial nerve, medulla spinalis, preganglionic symphathetic nerves that innervates the sweat glands, and the like. In some of these embodiments, the cholinergic cell is an amacrine cell. An "amacrine cell" is a class of neuron located in the inner nuclear layer or ganglion cell layer of the retina with processes parallel to the plane of the retina.

In other embodiments, e.g., where the transporter is VGAT, the target cell is a cell that expresses transiently on its surface a VGAT polypeptide, or a cell on which a VGAT polypeptide is transiently surface-accessible. GABAergic cells include, but are not limited to, inhibitory interneurons in neocortex, thalamus, striatum, cerebellum, and the like.

In other embodiments, e.g., where the transporter is a VGLUT, such as VGLUT, VGLUT2, or VGLUT3, the target cell is a cell that expresses transiently on its surface a VGLUT polypeptide, or a cell on which a VGLUT polypeptide is transiently surface-accessible. Cells that normally produce and express transiently on their cell surface are glutamatergic neurons, including excitatory neurons in neocortex, striatum, thalamus, hippocampus, brainstem, and the like.

In other embodiments, e.g., where the transporter is a VMAT, such as VMAT1 or VMAT 2, the target cell is a cell that expresses transiently on its surface a VMAT polypeptide, or a cell on which a VMAT polypeptide is transiently surface-accessible. Monoaminergic cells are located mostly but not only in the brainstem, e.g. serotonergic cells in the Raphe nucleus, noradrenergic cells in the locus cereleus, and dopaminergic cells in the *Substantia Nigra*.

Antibodies

An antibody that is suitable for use in an immunoselective agent of the invention is one that binds specifically to an epitope on a transporter polypeptide (e.g., a vesicular transporter), where the epitope is displayed on the surface of a neuronal cell that produces the transporter, and where the epitope, when displayed on the surface of the neuronal cell, is accessible to the antibody.

Any antibody that specifically binds a target transporter polypeptide antigen can be used in the production of an immunotoxin of the invention. By "specifically binds", as used herein, is meant an agent, such as an antibody, which binds a target antigen, but which does not substantially bind other molecules in a sample, e.g., a biological sample, which naturally includes other proteins. Generally, such an antibody specifically and selectively binds to a target antigen or peptide thereof.

Many suitable antibodies for use in the immunoselective targeting agents of the invention are commercially or otherwise publicly available. Furthermore, methods for production of antibodies that specifically bind a selected transporter polypeptide are well known in the art.

Transporter polypeptides suitable for use as immunogens include, but are not necessarily limited to, isolated transporter polypeptides; vesicular polypeptides associated with a membrane preparation, including a whole cell; fragments of at least about 6 amino acids of a transporter polypeptide; fusion proteins comprising transporter polypeptides, or fragments thereof; and the like. Vesicular transporter polypeptides are of particular interest.

Transporter polypeptides for raising antibodies can be prepared by mixing a transporter polypeptide that is to be used as an antigen with an adjuvant, and/or by making fusion proteins with larger immunogenic proteins. Target polypeptides (e.g., vesicular transporters) can also be covalently linked to other larger immunogenic proteins, such as keyhole limpet hemocyanin. Immunogens are typically administered intradermally, subcutaneously, or intramuscularly to experimental animals such as rabbits, sheep, and mice, to generate antibodies. Monoclonal antibodies can be generated by isolating spleen cells and fusing myeloma cells to form hybridomas.

Preparations of polyclonal and monoclonal antibodies specific for polypeptides encoded by a selected polynucleotide are made using standard methods known in the art. Typically, at least 6, 8, 10, or 12 contiguous amino acids are required to form an epitope. Epitopes that involve non-contiguous amino acids may require a longer polypeptide, e.g., at least 15, 25, or 50 amino acids.

Antibodies that specifically bind to a transporter polypeptide are generally those that provide a detection signal at least 5-, 10-, or 20-fold higher than a detection signal provided with an unrelated polypeptide, or with a cell that does not express the transporter used as an immunogen, when used in an assay, such as a cell surface binding assay; a competition assay; a Western blot; or other immunochemical assay. Generally, antibodies that specifically bind polypeptides of the invention do not bind to other proteins in immunochemical assays at detectable levels and can immunoprecipitate the specific polypeptide from solution.

An antibody that specifically binds a transporter polypeptide when it is surface-accessible on a neuronal cell that normally expresses the transporter polypeptide, and does not bind to neuronal cells that do not express the transporter polypeptide used as an immunogen. Whether an antibody is specific for a transporter, and binds the transporter when it is accessible on the surface of a neuronal cell that normally produces the transporter can be determined using a cell surface staining method.

Methods of determining whether an antibody binds an epitope when accessible on the surface of a cell are well known in the art. Such methods generally involve contacting the cell with an antibody being tested, and subjecting the cell to any of a variety of assays, including, but not limited to, fluorescence activated flow cytometry; immunocytochemistry; fluorescence microscopy; and the like. Generally, an antibody being tested is labeled (either directly or indirectly), and used to stain the surface of a neuronal cell that normally produces the transporter. Direct labels include fluorescent labels and the like that are attached to an antibody. Direct labels include radioisotopes (e.g., $^{125}$I; $^{35}$S, and the like); enzymes whose products are detectable (e.g., luciferase, β-galactosidase, horse radish peroxidase, and the like); fluorescent labels (e.g., fluorescein isothiocyanate, rhodamine, phycoerythrin, and the like); fluorescence emitting metals, e.g., $^{152}$Eu, or others of the lanthanide series, attached to the antibody through metal chelating groups such as EDTA; chemiluminescent compounds, e.g., luminol, isoluminol, acridinium salts, and the like; bioluminescent compounds, e.g., luciferin; fluorescent proteins; and the like. Indirect labels include secondary antibodies (e.g., where the primary antibody is a rat antibody, a goat anti-rat Ig antibody) that are labeled with a fluorescent dye or other type of detectable label; labeled proteins that bind immunoglobulin (e.g., protein A); and labeled members of a specific binding pair (e.g., biotin/avidin where the primary antibody is conjugated to biotin and avidin is detectably labeled); and the like. The presence of specific staining indicates that the antibody is both specific and binds the transporter polypeptide when it is surface-accessible on a neuronal cell that normally expresses the transporter polypeptide.

As noted above, "antibody" or "immunoglobulin" encompasses various kinds of antibodies, including, but not necessarily limited to, naturally occurring antibodies, single domain antibodies, hybrid antibodies, chimeric antibodies, single-chain antibodies, and antibody fragments that retain antigen binding specificity, and the like. Antibodies can be of any class (e.g., IgM, IgG, IgA, IgE; frequently IgG). Naturally occurring antibodies specific for target antigen polypeptides, can be obtained according to methods well known in the art. For example, serum antibodies to a polypeptide of the invention in a human population can be purified by methods well known in the art, e.g., by passing antiserum over a column to which target antigen, or the corresponding fusion protein, is bound. The bound antibodies can then be eluted from the column, for example using a buffer with a high salt concentration.

For preparation of polyclonal antibodies, the first step is immunization of the host animal with the target protein, where the target protein will preferably be in substantially pure form, e.g., comprising less than about 1% contaminant. The immunogen may comprise the complete target protein, fragments or derivatives thereof. To increase the immune response of the host animal, the target protein may be combined with an adjuvant, where suitable adjuvants include alum, dextran, sulfate, large polymeric anions, oil and water emulsions, e.g. Freund's incomplete adjuvant, Freund's complete adjuvant, and the like. The target protein may also be conjugated to synthetic carrier proteins or synthetic antigens. A variety of hosts may be immunized to produce the polyclonal antibodies. Such hosts include rabbits, guinea pigs, rodents, e.g. mice, rats, sheep, goats, and the like. The target protein is administered to the host, usually intradermally, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAE chromatography, and the like.

Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include mouse, rat, hamster, etc. To raise antibodies against the human protein, the animal will generally be a mouse, rat, hamster, guinea pig, rabbit, etc. The antibody may be purified from the hybridoma cell supernatants or ascites fluid by conventional techniques, e.g. affinity chromatography using protein according to the subject invention bound to an insoluble support, protein A sepharose, etc.

The invention also encompasses single domain antibodies, hybrid antibodies, chimeric antibodies, single-chain antibodies, and antibody fragments that retain antigen binding specificity. As used herein, a "single domain antibody" (dAb) is an antibody which is comprised of an VH domain, which reacts immunologically with a designated antigen. A dAb does not contain a $V_L$ domain, but may contain other antigen binding domains known to exist in antibodies, for example, the kappa and lambda domains. Methods for preparing dAbs are known in the art. Antibodies may also be comprised of $V_H$ and $V_L$ domains, as well as other known antigen binding domains. Examples of these types of antibodies and methods for their preparation are known in the art (see, e.g., U.S. Pat. No. 4,816,467, which is incorporated herein by reference), and include the following.

"Vertebrate antibodies" refers to antibodies which are tetramers or aggregates thereof, comprising light and heavy chains which are usually aggregated in a "Y" configuration and which may or may not have covalent linkages between the chains. In vertebrate antibodies, the amino acid sequences of all the chains of a particular antibody are homologous with the chains found in one antibody produced by the lymphocyte which produces that antibody in situ, or in vitro (for example, in hybridomas). Vertebrate antibodies typically include native antibodies, for example, purified polyclonal antibodies and monoclonal antibodies. Examples of the methods for the preparation of these antibodies are described infra.

"Hybrid antibodies" are antibodies wherein one pair of heavy and light chains is homologous to those in a first antibody, while the other pair of heavy and light chains is homologous to those in a different second antibody. Typically, each of these two pairs will bind different epitopes, particularly on different antigens. This results in the property of "divalence", i.e., the ability to bind two antigens simultaneously. Such hybrids may also be formed using chimeric chains, as set forth below.

"Chimeric antibodies", are antibodies in which the heavy and/or light chains are fusion proteins. Typically the constant domain of the chains is from one particular species and/or class, and the variable domains are from a different species and/or class. Also included is any antibody in which either or both of the heavy or light chains are composed of combinations of sequences mimicking the sequences in antibodies of different sources, whether these sources be differing classes, or different species of origin, and whether or not the fusion point is at the variable/constant boundary. Thus, antibodies can be produced in which neither the constant nor the variable region mimic known antibody sequences, thus providing for antibodies having a variable region that has a higher specific affinity for a particular antigen, or having a constant region that can elicit enhanced complement fixation, or to make other improvements in properties possessed by a particular constant region.

The invention also encompasses "altered antibodies", which refers to antibodies in which the naturally occurring amino acid sequence in a vertebrate antibody has been vaned. Utilizing recombinant DNA techniques, antibodies can be redesigned to obtain desired characteristics. The possible variations are many, and range from the changing of one or more amino acids to the complete redesign of a region, for example, the constant region. Changes in the constant region, in general, to attain desired cellular process characteristics, e.g., changes in complement fixation, interaction with membranes, and other effector functions. Changes in the variable region may be made to alter antigen-binding characteristics. The antibody may also be engineered to aid the specific delivery of a molecule or substance to a specific cell or tissue site. The desired alterations may be made by known techniques in molecular biology, e.g., recombinant techniques, site directed mutagenesis, and other techniques.

Further exemplary antibodies include "univalent antibodies", which are aggregates comprised of a heavy chain/light chain dimer bound to the Fe (i.e., constant) region of a second heavy chain. This type of antibody escapes antigenic modulation. See, e.g., Glennie et al. (1982) Nature 295: 712–714.

Included also within the definition of antibodies are "Fab" fragments of antibodies. The "Fab" region refers to those portions of the heavy and light chains which are roughly equivalent, or analogous, to the sequences which comprise the branch portion of the heavy and light chains, and which have been shown to exhibit immunological binding to a specified antigen, but which lack the effector Fe portion. "Fab" includes aggregates of one heavy and one light chain (commonly known as Fab'), as well as tetramers containing the 2H and 2L chains (referred to as F(ab)$_2$), which are capable of selectively reacting with a designated antigen or antigen family. "Fab" antibodies may be divided into subsets analogous to those described above, i.e., "vertebrate Fab", "hybrid Fab", "chimeric Fab", and "altered Fab". Methods of producing "Fab" fragments of antibodies are known within the art and include, for example, proteolysis, and synthesis by recombinant techniques.

Suitable antibodies can be raised to a peptide corresponding to a surface-accessible portion of the transporter. Peptides of from about 5 amino acids to about 50 amino acids are linked to a moiety, such as a larger protein or other substance (e.g., a solid support), and the linked peptide is introduced into a mammalian host. Antibodies are isolated using techniques well known to those skilled in the art.

An exemplary target transporter is the vesicular transporter protein VAChT and an exemplary antibody is an anti-VAChT antibody. An exemplary anti-VAChT antibody is available from Chemicon International (Temecula, Calif.). Anti-VAChT antibodies can also be custom produced. An example of a suitable anti-VAChT antibody is one raised to a fragment of amino acids 511–530 of a VAChT polypeptide.

Commercially available anti-transporter antibodies (e.g., anti-vesicular transporter antibodies) can be obtained from, for example, Promega Corp. (Madison, Wis.); BioMol Research Laboratories, Inc. (Plymouth Meeting, Pa.); PharMingen (San Diego, Calif.); Sigma (St. Louis, Mo.); Progen; Research Genetics; Alpha Diagnostics International (San Antonio, Tex.); Eurodiagnostica; ICN Biomedicals, Inc.; Biotrend Chemikalien GmbH; Accurate Chemical and Scientific; and Oncogene Research Products.

Cytotoxins

Any of a variety of cytotoxins are suitable for use in the immunotoxins of the present invention, which are readily available (e.g., commercially available). Cytotoxins may be isolated from a natural source (e.g., naturally-occurring), recombinantly produced, or synthetically produced. Cytotoxins include ribosome inactivating proteins (RIPs); photoactivatable cytotoxins; a vinca alkaloid; an anthracycline; a bacterial toxin; and the like.

Cytotoxins of particular interest are RIPs a class of proteins ubiquitous in higher plants having activity as potent inhibitors of eukaryotic protein synthesis. In general, RIPs, which are divided into Type I and Type II classes, hydrolytically cleave an N-glycosidic bond of a specific adenine base in a highly conserved loop region of the 28S rRNA of eukaryotic ribosomes, thereby inactivating translation. See, e.g., U.S. Pat. No. 5,744,580. Type I RIPS are composed of a single peptide chain having ribosome-inactivating activity, while Type II proteins are composed of an A-chain, essentially equivalent to a Type I protein, disulfide-linked to a B-chain having cell-binding properties.

Exemplary Type I RIPS of interest in the present invention include, but are not necessarily limited to, gelonin, dodecandrin, tricosanthin, tricokirin, bryodin, Mirabilis antiviral protein (MAP), barley ribosome-inactivating protein (BRIP), pokeweed antiviral proteins (PAPS), saporins, luffins, and momordins. Exemplary Type II RIPS of interest in the present invention include, but are not necessarily limited to, ricin and abrin. In some embodiments of particular interest, the cytotoxin is saporin.

In addition to cytotoxins having wild-type amino acid sequences, variants of such cytotoxins, including, but not limited to, analogs, mutants (e.g., cytotoxins have amino acid sequences that differ from wild-type by addition, deletion, and/or substitution of one or more amino acids), fusion proteins, and the like, providing the cytotoxin retains a desired activity in killing of a desired target cell.

Other suitable cytotoxins include, but are not limited to, plant alkaloids such as the vinca alkaloids vinblastine, vindesine, and vincristine (see, e.g., U.S. Pat. No. 4,522,750); an anthracycline such as doxorubicin (see, e.g., U.S. Pat. Nos. 5,547,667; 5,776,458; 5,122,368; and 5,622,929); phototoxins, as are known in the art (see, e.g., U.S. Pat. Nos. 4,612,007; 4,613,322; 4,684,521; and 5,670,151); bacterial toxins, as are known in the art (see, e.g., U.S. Pat. Nos. 5,352,447; 5,208,021; 5,792,458; and 6,099,842), and invertebrate toxins (e.g. bee toxin, scorpion venom toxins, snake venom toxins, jelly fish toxins, puffer fish toxins, and the like).

Substances that Increase Cell Survival

Any of a variety of substances that increase cell survival are suitable for use in the immunoselective agents of the inveiton. Exemplary cell survival-promoting substances includes, for example, cytokines, growth factors, protease inhibitors, hormones, and the like.

Specifically exemplary substances that promote or increase cell survival include, but are not limited to, (R)-N-(2-heptyl)methyl-propargylamine (R-2HMP; Durden et al. (2000) *Drug Metabl. Distr.* 28:147–154); an aliphatic propargylamine (see, e.g., U.S. Pat. No. 6,251,950); a deprenyl compound, e.g., R-deprenyl HCl, and desmethyldeprenyl; N-acetylcysteine (see, e.g., U.S. Pat. No. 6,417,160); a serine protease inhibitor; insulin-like growth factor; a caspase inhibitor (see, e.g., U.S. Pat. No. 6,355,618); an interleukin-1β converting enzyme (ICE) inhibitor (see, e.g., WO 93/05071; WO 96/03982; WO 00/01666; U.S. Pat. No. 5,585,357); bcl-2; Bcl-x1; Mcl-1; Bak; A1; A20; TNF-α; nerve growth factor; epidermal growth factor; 3-aminobenzamide; aphidocolin; L-ascorbic acid; catalase; follicle stimulating hormone; vasoactive intestinal peptide; cyclic GMP; hCG; interleukin-1β; superoxide dismutase; aurintricarboxylic acid; BAPTA/AM; caffeine; calpain inhibitor I; calpain inhibitor II; leupeptin; N-ethyl maleimaide; cyclosporin A; acetyl-leucyl-leucyl-normethional; 3,4-dichloroisocoumarin; diisopropylfluorophosphate; phenylmethylsulfonyl fluoride; tetrodotoxin; nimodipine; verapamil; flunarizine; R56865; forskolin; genistein; herbimycin A; interleukin-6; calyculin A; okadaic acid; calyculin A; phorbol-12-myristate-13-acetate; 1-Pyrrolidinecarbodithioic acid; nifedipine; nisoldipine; aurintricarboxylic acid; spermine; thioredoxin, N-alpha-Tosyl-L-Phe chloromethyl ketone; and N-alpha-Tosyl-L-Lys chloromethyl ketone; and a substance that increases production in a cell of a factor that promotes cell survival, where factors that promote cell survival include, but are not limited to, survivin; Other exemplary cell survival-promoting substances can include anti-sense RNA and small interfering RNAs.

Suitable cell survival promoting agents are those that, when delivered to the cytoplasm of a cell, increase cell survival by at least about 20%, at least about 30%, at least about 40%, at least about 50%, at least about 2-fold, at least about 4-fold, at least about 10-fold, or more, compared with a cell not containing the agent. Whether a given agent promotes or increases cell survival can be determined using any known method for assessing anti-apoptotic activity, including the methods described below. For example, a cell is contacted with an apoptosis-inducing agent and an agent that promotes cell survival, and the effect of the cell survival promoting agent on cell survival is assessed using an assay for apoptosis.

Additional Components

In some embodiments, an immunoselective targeting agent of the invention further comprises a detectable label bound to the antibody portion of the immunoselective targeting agent.

Suitable detectable labels include radioisotopes (e.g., $^{125}$I; $^{35}$S, and the like); enzymes whose products are detectable (e.g., luciferase, β-galactosidase, horse radish peroxidase, and the like); fluorescent labels (e.g., fluorescein isothiocyanate, rhodamine, phycoerythrin, and the like); fluorescence emitting metals, e.g., $^{152}$Eu, or others of the lanthanide series, attached to the antibody through metal chelating groups such as EDTA; cyanine dyes; chemiluminescent compounds, e.g., luminol, isoluminol, acridinium salts, and the like; bioluminescent compounds, e.g., luciferin; fluorescent proteins; and the like. Fluorescent proteins include, but are not limited to, a green fluorescent protein (GFP), including, but not limited to, a "humanized" version of a GFP, e.g., wherein codons of the naturally-occurring nucleotide sequence are changed to more closely match human codon bias; a GFP derived from *Aequoria Victoria* or a derivative thereof, e.g., a "humanized" derivative such as Enhanced GFP, which are available commercially, e.g., from Clontech, Inc.; a GFP from another species such as *Renilla reniformis, Renilla mulleri*, or *Ptilosarcus guernyi*, as described in, e.g., WO 99/49019 and Peelle et al. (2001) *J. Protein Chem.* 20:507–519; "humanized" recombinant GFP (hrGFP) (Stratagene); any of a variety of fluorescent and colored proteins from Anthozoan species, as described in, e.g., Matz et al. (1999) *Nature Biotechnol.* 17:969–973; and the like.

Method of Making Immunoselective Targeting Agents of the Invention

Subject immunoselective targeting agents include one or more molecules of a substance linked to an antibody, e.g., a subject immunoselective targeting agent comprises from one to about 10 molecules, e.g., from one to about 4, from about 4 to about 6, or from about 6 to about 10 molecules of a substance linked to a single antibody polypeptide.

The method of linking the substance being delivered (e.g., the cytotoxic compound or cell survival-promoting compound) to the antibody will depend, in part, on the functional group(s) available on the substance being delivered.

In some embodiments, the linkage is a covalent linkage. In other embodiments, the linkage is a non-covalent linkage. Suitable linkages include cleavable and non-cleavable linkages.

In some embodiments, the linkage is a non-cleavable linkage. Examples of non-cleavable linker systems which can be used in this invention include the carbodiimide (EDC), the sulfhydryl-maleimide, the N-succinimidyl-3-(2-pyridyldithio) propionate (SPDP; Pharmacia), and the periodate systems.

In other embodiments, the linkage is a cleavable linkage. Cleavable linkers include, but are not limited to, the acid labile linkers described in U.S. Pat. No. 5,144,011. Acid labile linkers include, but are not limited to, cis-aconitic acid, cis-carboxylic alkadienes, cis-carboxylic alkatrienes, and poly-maleic anhydrides. Other cleavable linkers are linkers capable of attaching to primary alcohol groups.

In some embodiments, the substance being delivered is linked directly to the antibody. In other embodiments, the substance being delivered is linked indirectly, e.g., through a linker, to the antibody. A linker may be an organic, inorganic, or semi-organic molecule, and may be a polymer of an organic molecule, an inorganic molecule, or a co-polymer comprising both inorganic and organic molecules.

Where the substance being linked to the antibody contains, or is derivatized to contain, a sulfhydryl group, the linkage between the substance and the antibody can be made using a bifunctional agent, such as maleimidobenzoyl sulfosuccinimide. Where the substance being linked to the antibody comprises a lysine residue, N-hydroxysuccinimide can be used.

Linkage of a substance to an antibody may be made using a variety of bi-functional protein coupling agents. Examples of such reagents are N-succinimidyl-3-(2-pyridyldithio) propionate (SPDP), iminothiolane (IT), bi-functional derivatives of imidoesters such as dimethyl adipimidate HCl, active esters such as disuccinimidyl suberate, aldehydes such as glutaraldehyde, bis-azido compounds such as bis(p-diazoniumbenzoyl)-ethylenediamine, diisocyanates such as tolylene 2,6-diisocyante, and bis-active fluorine compounds such as 1,5-fluoro-2,4-dinitrobenzene.

An exemplary, non-limiting, agent used to covalently attach a substance to an antibody is 1-ethyl-3[3-dimethylaminopropyl] carbodiimide hydrochloride (EDC). EDC is particularly useful in those embodiments in which the substance being linked to the antibody is a polypeptide. In these embodiments, EDC is a useful agent because of the occurrence of amino acid residues with amino- and carboxyl-groups in both the antibody and the substance being linked to the antibody molecules. Carbodiimides such as EDC are carboxyl and amine reactive, and thus couple carboxyls to primary amines or hydrazides, resulting in formation of amide or hydrazone bonds. A carbodiimide bond can thus be formed between the carboxy groups of the substance being linked and the amino groups of the antibody molecule.

Carbodiimides are unlike other conjugation reactions in that no cross-bridge is formed between the molecules being coupled. Carboxy termini of proteins can be targeted, as well as glutamic and aspartic acid side chains. In the presence of excess cross-linker, polymerization is likely to occur because proteins contain carboxyls and amines. Since no cross-bridge is formed, and the amide bond is the same as a peptide bond, so reversal of the cross-linking is impossible without destruction of the protein. EDC (Pierce Co.) reacts with carboxylic acid groups and activates the carboxyl group, allowing it to be coupled to the amino group in the reaction mixture.

In general, the EDC reaction is accomplished in a single step by mixing the cytotoxin of interest, the antibody of interest, and an effective amount of EDC, and incubating at room temperature. In general, the antibody and cytotoxin are provided in the reaction mixture in equal parts. The ratio of reactants in the mixture can be varied according to the desired product. For example, where an immunotoxin having fewer cytotoxin molecules attached is desired, the ratio of cytotoxin to antibody is decreased. Where an immunotoxin having a greater number of cytotoxin molecules is desired, then the ratio cytotoxin to antibody is increased.

Typically antibody and toxin are mixed in equimolar ratios in the presence of a catalytic amount of EDC. The number of toxin molecules attached to each antibody molecule can be increased by mixing 2-fold, 3-fold, 4-fold, 5-fold, or 6-fold or more excess toxin relative to antibody in the presence of EDC. For example, since each antibody has the capacity of taking on six saporin molecules without encountering steric hinderance, antibody can be mixed with up to about six-fold saporin to provide for maximum toxin: antibody in the immunotoxin. The absolute amounts of the antibody and toxin can be varied to suit the desired end product, e.g. 10 μg, 50 μg, 200 μg, 200 mg to 1 g of each component and in various combinations.

FIG. 1A provides a schematic of the structure of an exemplary antibody (an anti-VAChT antibody) conjugated to an exemplary cytotoxin (saporin) by use of EDC. The immunotoxin can be produced so that the antibody is conjugated to at least 1, usually at least 2, more usually at least 3, generally at least 4, more generally at least 5, and up to 6 cytotoxin molecules. The number of cytotoxin molecules present in an immunotoxin of the invention will vary according to such factors as, for example, the molecular weight and structure of the cytotoxin, and the relative size of the antibody molecule to which it is to be conjugated. As illustrated in FIG. 1A, mass ratio analysis indicates that up to about 6 saporin molecules can be attached to a single IgG molecule without steric hindrance.

The length of the EDC reaction can be controlled to optimize multimerization the anti-VAChT-saporin complex, and thus the quantity of saporin delivered by a single binding reaction can be high.

Figure 1B:
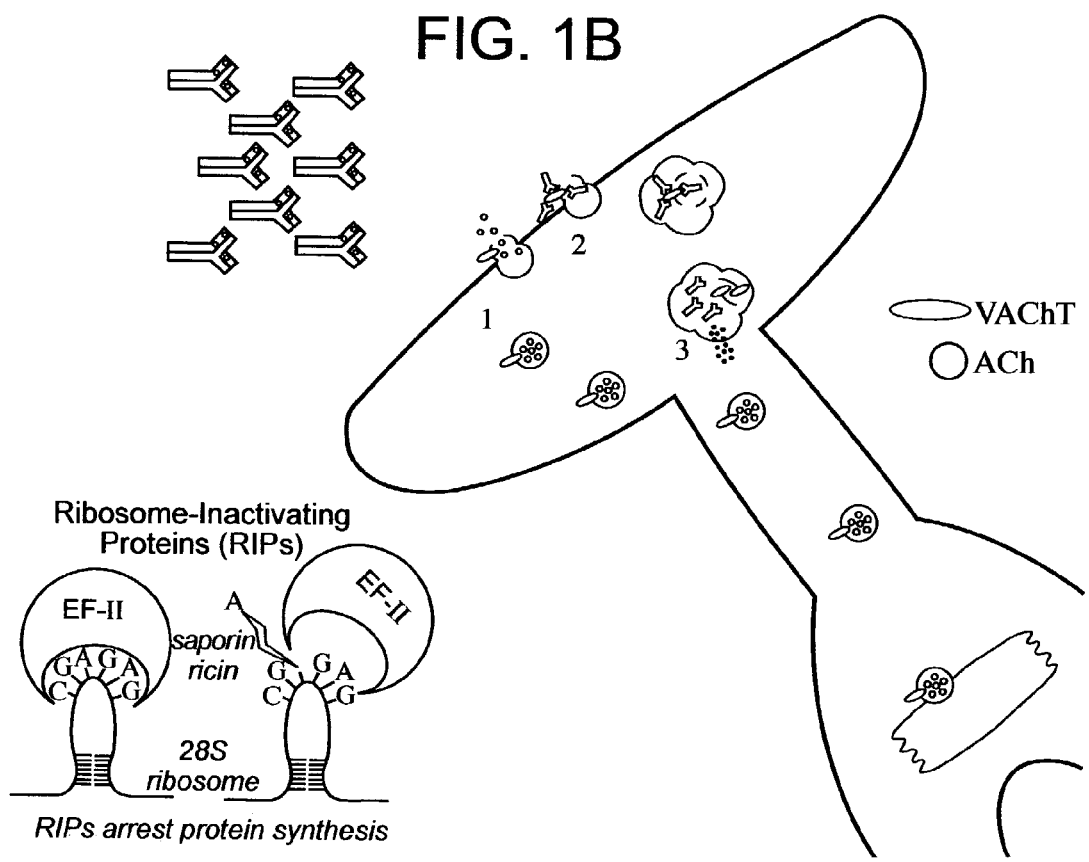
FIG. 1B is a schematic illustration of the possible mechanism of action by which the immunotoxin kills cholinergic amacrine cells by arresting protein synthesis.

Without being held to theory, the transport of Ach and VAChT to the cell surface during release of neurotransmitter exposes the VAChT antigen to anti-VAChT-saporin (Matteoli et al., 1992 *J. Cell Biol.* 117:849–61) is depicted in FIG. 1B. Vesicular recycling provides ingress of the ribosome-inactivating protein toxin to the cell, while endosomal processing causes its subsequent release. The insert in FIG. 1B represents the "translational poisoning" mechanism ascribed to the RIPs (Girbes et al., 1996 *Cell. Mol. Biol.* 42(4):461–471). This family of proteins, which includes ricin and saporin, has a highly specific N-glycosidase activity that removes an adenine molecule from the elongation factor II (EF II) binding domain of the 28S ribosomal RNA (A4324 in the rat). This results in the suspension of protein synthesis and rapid cyotoxicity due to cessation of nascent peptide elongation.

Properties of Subject Immunoselective Targeting Agents

Immunoselective agents of the invention selectively bind a transporter (e.g., a vesicular transporter) that is surface-accessible on a neuronal cell. An immunoselective agent of the invention selectively delivers a substance to a neuronal cell on which a transporter (e.g., a vesicular transporter) is transiently surface-accessible, e.g., the substance is delivered selectively to the cytoplasm of target neuronal cells. Thus, an immunoselective agent of the invention provides for selective delivery of a substance to a neuronal cell, e.g., less than about 10%, less than about 8%, less than about 6%, less than about 4%, less than about 2%, less than about 1%, less than about 0.5%, or less than about 0.01% of the cells in a population of cells that acquire the substance in their cytoplasm are non-target cells.

Where an immunoselective agent of the invention is an immunotoxin, the immunotoxin is an "ideal" immunotoxin in that it can be characterized by having two key properties, and thus provides for unexpected advantages over conventional immunotoxins. First, it is effective in completely eliminating the targeted cell population, and second, the effect is selective, so that other cell types are not destroyed directly by its action.

First, the immunotoxin of the invention can provide for selective and efficient killing of target cells. For example, the immunotoxin of the invention can provide for killing of at least 50%, at least 75%, at least 85%, at least 90%, or at least-95% or more up to 100% of target cells following contact of the immunotoxin with the target cell. These levels of killing can be observed in a significantly shorter time frame than with conventional immunotoxins. For example, at least about 50% of target cells, and in some case at least about 85–90% of target cells, are killed within a few hours (e.g., within about 24 hrs, within about 48 hrs, or within about 72 hrs) or within a few days (e.g., within about 1 day, within about 2 days, within about 5 days, within about 10 days, and in less than 14 days).

An immunotoxin of the invention further provides for selective killing of the target cell. For example, of the cells killed by contacting the immunotoxin with a mixed cell population (e.g., either in vivo or in vitro, e.g., in animal models observed by biopsy, in tissue sections, or in mixed cell culture) less than about 10%, less than about 5%, or less than about 1% of cells killed are non-target cells. Preferably, killing of non-target cells in the mixed cell population of target cells and non-target cells is not detectable (i.e., the level of killing of non-target cells by the immunotoxin is so low as to be below detection by, for example, immunofluorescence techniques).

The advantages of the immunoselective targeting agents of the invention are further enhanced where the target antigen is a transporter molecule, particularly a vesicular transporter. Without being held to theory, the transporter molecule increases the efficiency of uptake of the cytotoxin by the target cells. The advantages of the immunoselective targeting agents of the invention are still further enhanced where the substance being delivered is one that is potent. For example, quantification of the killing power of immunotoxins has shown that fewer than 1000 molecules of saporin are adequate to produce death (Kreitman and Pastan, 1998 *Cancer Res.* 58(5):968–975). Use of EDC coupling provides an additional advantage in that the length of the reaction can be controlled to optimize multimerization of the immunotoxin complex, and thus the quantity of cytotoxin delivered by a single binding reaction. In addition to the effects of any bound cytotoxin, binding of antibody to transporter protein itself also damages the target cells. For example, antibody binding to vesicular transporters can corrupt the endocytosis of neurotransmitter in to the vesicle.

Anti-VAChT Immunotoxin

In one embodiment of particular interest, the immunotoxin has activity in selective depletion of cholinergic neuronal cells. In this embodiment, the immunotoxin comprises an antibody that specifically binds a vesicular acetylcholine transporter (VAChT), which is covalently attached to a cytotoxin, preferably saporin. Following binding of the immunotoxin on cholinergic cells, the immunotoxin is internalized and, once inside the cell, facilitates killing of the cholinergic neuron.

Use of the VAChT receptor takes advantage of the biology of vesicular recycling. Acetylcholine (ACh) is produced in the cytosol by ChAT and then transported into small synaptic vesicles by VAChT. Upon release of ACh, the component proteins of these vesicles, including VAChT, are exposed at the cell surface by fusion of the vesicle with the plasma membrane. The vesicle component proteins are then recycled from the plasma membrane by clathrin-dependent endocytosis via an endosomal compartment. Matteoli et al. (1992) showed that it is possible to label synaptic vesicles with antibodies to the luminal domain of the vesicle protein, synaptotagmin I, and that antibodies presented at the cell surface undergo endocytosis and recycling along with vesicle proteins. In that study, a general endocytosis-lysosomal pathway marker, wheat germ agglutinin, was rapidly cleared from neuronal processes.

Anti-VAChT immunotoxins are of particular interest as research reagents, and in this context have many applications as such a reagent. In one embodiment, the anti-VAChT immunotoxin is injected intraocularly in an animal model to examine the role and influence of cholinergic neurons in retinal development. Cholinergic amacrine cells are present on the day of birth in the developing rat. As illustrated below, a single intraocular injection of anti-VAChT-saporin at postnatal day 1 resulted in a rapid and complete loss of cholinergic amacrine cells, while other retinal cell types were not affected by the treatment. Through the use of the anti-VAChT immunotoxin reagent, it was determined that depletion of cholinergic amacrine cells does not affect the subsequent formation of the segregated projections of On and Off cone bipolar cells. Thus, selective depletion of the cells using VAChT-saporin leaves the remaining cells intact structurally as well as functionally. This finding was an unexpected advantage of using the VAChT-saporin construct.

In the Examples section below, experimental evidence demonstrates the advantage that an anti-VAChT immunotoxin made according to the invention can be used to achieve a relatively rapid and complete elimination of a target cell, without any apparent non-specific damage to the nearby cells. The target cells in these examples were cholinergic amacrine cells, with the target antigen being the transporter molecule vesicular acetylcholine transporter. In the specific example, the cytotoxin of the immunotoxin was saporin. This immunotoxin is generally referred to herein as an example of an anti-VAChT immunotoxin.

The anti-VAChT immunotoxin demonstrated efficient killing of target cells, since even at relatively low doses all cholinergic amacrine cells were eliminated after a single treatment. Moreover, this effect occurred quite rapidly, with most cells being eliminated within 48 hours after the intraocular administration by the immunotoxin. Other immunotoxins have been reported to take much longer to destroy cells, in some cases, as much as 14 days after treatment (e.g., Martin et al., 1999). With respect to the specificity of the effects, counts of all cells in the ganglion cell layer, as well as On and Off cone bipolar cells and dopaminergic amacrine cells showed that these populations were all within normal limits.

In addition, the anti-VAChT immunotoxin exemplifies the advantage that can be gained by use of a transporter molecule as a target antigen. The use of transporter molecules avoids the loss of immunotoxin toxicity that has been attributed to receptor endocytosis followed by lysosomal degradation (Davol et al., 1999 *Anticancer Res.* 19(3A): 1705–1713). In addition to this endosomal targeting strategy, the multiple amide bonds linking antibodies and saporin resulted in a stable compound that facilitated efficient target-cell killing.

Upon reading the present specification, one of ordinary skill in the art can readily extend the rationale used in the design and production of anti-VAChT immunotoxin to other cell types defined on the basis of their neurotransmitter or neuromodulator content.

Compositions

The invention further provides compositions comprising an immunoselective targeting agent of the invention. Compositions generally include an immunoselective targeting agent and a buffer. In some embodiments, a subject composition comprises an immunoselective targeting agent and a pharmaceutically acceptable excipient. Those skilled in the art can readily select an appropriate buffer, a wide variety of which are known in the art, suitable for an intended use. In some instances, the composition can comprise a pharmaceutically acceptable excipient, a variety of which are known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

Immunoselective targeting agents of the present invention may be formulated in any manner suitable for the target cell and the route of administration, as well as the environment in which the immunotoxin is to be used (e.g., in vivo, in vitro, ex vivo). In general, the immunotoxin is provided in combination with a pharmaceutically acceptable excipient (e.g., saline, buffered saline (PBS), and the like) in a concentration that provides for delivery of an effective dose (e.g., an amount effective to accomplish killing of a desired number of target cells, or an amount effective to reduce cell death).

A formulation containing a therapeutically effective amount of an immunoselective agent can be provided as sterile liquid solutions, liquid suspensions, or lyophilized versions, and can further include stabilizers or excipients. Lyophilized compositions are reconstituted with suitable diluents, e.g., water for injection, saline, 0.3% glycine and the like, at a level of about from 0.01 mg/kg of host body weight to 10 mg/kg where the biological activity is less than or equal to 20 ng/ml when measured in a reticulocyte lysate assay.

For example, an immunoselective targeting agent can be prepared as an injectable or topical preparation. Parental formulations are known and are suitable for use in the invention, e.g., for intraocular, intracranial, intramuscular, intravenous, subcutaneous, intradermal, and other parenteral routes of administration.

Where the immunoselective targeting agent is an immunotoxin, the pharmaceutical compositions containing an immunotoxin are contacted with target cells in an amount effective to provide for selective killing of target cells with minimal or no killing of non-target cells, and preferably without significant or detectable damage to non-target cells. For therapeutic applications, the immunotoxins of the invention are administered in a therapeutically effective dose in a range of from about 0.01 mg/kg to about 5 mg/kg of the patient. An exemplary, therapeutically effective dose of the pharmaceutical composition containing an immunotoxin of the invention is in a range of from about 0.01 mg/kg to about 0.5 mg/kg body weight of the patient administered over several days to two weeks by daily intravenous infusion, each given over a one hour period, in a sequential patient dose-escalation regimen.

Compositions according to the invention may be formulated into topical preparations for local therapy by including a therapeutically effective concentration of immunoselective targeting agent in a dermatological vehicle. The amount of immunoselective targeting agent to be administered, and the immunoselective targeting agent concentration in the topical formulations, depend upon the vehicle selected, the clinical condition of the patient, the systemic toxicity and the stability of the immunoselective targeting agent in the formulation. Thus, a physician knows to employ the appropriate preparation containing the appropriate concentration of immunoselective targeting agent in the formulation, as well as the appropriate amount of formulation to administer depending upon clinical experience with the patient in question or with similar patients.

The concentration of immunoselective targeting agent for topical formulations is in the range of greater than from about 0.1 mg/ml to about 25 mg/ml. Typically, the concentration of immunoselective targeting agent for topical formulations is in the range of greater than from about 1 mg/ml to about 20 mg/ml. Solid dispersions of immunoselective targeting agents according to the invention, as well as solubilized preparations, may be used. Thus, the precise concentration to be used in the vehicle is subject to modest experimental manipulation in order to optimize the therapeutic response. For example, greater than about 10 mg immunoselective targeting agent/100 grams of vehicle may be useful with 1% w/w hydrogel vehicles in the treatment of skin inflammation. Suitable vehicles, in addition to gels, are oil-in-water or water-in-oil emulsions using mineral oils, petroleum and the like.

An immunoselective targeting agent according to the invention may be optionally administered topically by the use of a transdermal therapeutic system Barry, "Dermatological Formulations," p. 181 (1983) and literature cited therein. While such topical delivery systems may have been designed for transdermal administration of low molecular weight drugs, they are capable of percutaneous delivery. Further, such systems may be readily adapted to administration of immunoselective targeting agent or derivatives thereof and associated therapeutic proteins by appropriate selection of the rate-controlling microporous membrane.

Topical preparations of immunoselective targeting agent either for systemic or local delivery may be employed and may contain excipients as described above for parenteral administration and other excipients used in a topical preparation such as cosolvents, surfactants, oils, humectants, emollients, preservatives, stabilizers and antioxidants. Pharmacologically-acceptable buffers may be used, e.g., Tris or phosphate buffers. The topical formulations may also optionally include one or more agents variously termed enhancers, surfactants, accelerants, adsorption promoters or penetration enhancers, such as an agent for enhancing percutaneous penetration of the immunotoxin or other agents. Such agents should desirably possess some or all of the following features as would be known to the ordinarily skilled artisan: pharmacological inertness, non-promotive of body fluid or electrolyte loss, compatible with immunoselective targeting agent (non-inactivating), and capable of formulation into creams, gels or other topical delivery systems as desired.

An immunoselective targeting agent according to the present invention may also be administered by aerosol to achieve localized delivery to the lungs. This is accomplished by preparing an aqueous aerosol, liposomal preparation or solid particles containing immunotoxin. Ordinarily, an aqueous aerosol is made by formulating an aqueous solution or suspension of an immunoselective targeting agent together with conventional pharmaceutically acceptable carriers and stabilizers. The carriers and stabilizers vary depending upon the requirements for the particular immunoselective targeting agent, but typically include: nonionic surfactants (Tweens, Pluronics, or polyethylene glycol); innocuous proteins like serum albumin, sorbitan esters, oleic acid, lecithin; amino acids such as glycine; and buffers, salts, sugars or sugar alcohols. The formulations may also include mucolytic agents as well as bronchodilating agents. The formulations are sterile. Aerosols generally are prepared from isotonic solutions. The particles optionally include normal lung surfactants.

Alternatively, an immunoselective targeting agent of the invention may be administered orally by delivery systems such as proteinoid encapsulation as described by Steiner, et al., U.S. Pat. No. 4,925,673, incorporated by reference herein. Typically, a therapeutically-(effective oral dose of an immunoselective targeting agent according to the invention is in the range from about 0.05 mg/kg body weight to about 50 mg/kg body weight per day. An exemplary effective dose is in the range from about 0.05 mg/kg body weight to about 5 mg/kg body weight per day.

An immunoselective targeting agent according to the present invention may be administered systemically, rather than topically, by injection intramuscularly, subcutaneously, intrathecally or intraperitoneally or into vascular spaces, or into the joints, e.g., intraarticular injection at a dosage of greater than about 1 µg/cc joint fluid/day. The dose will be dependent upon the properties of the specific immunoselective targeting agent employed, e.g., its activity and biological half-life, the concentration of immunoselective targeting agent in the formulation, the site and rate of dosage, the clinical tolerance of the patient involved, the disease afflicting the patient and the like, as is well within the skill of the physician.

An immunoselective targeting agent of the present invention may be administered in solution. The pH of the solution is generally in the range of pH 5 to 9.5, e.g., pH 6.5 to 7.5. The immunoselective targeting agent or derivatives thereof should be in a solution having a suitable pharmaceutically-acceptable buffer such as phosphate, Tris (hydroxymethyl) aminomethane-HCl or citrate and the like. Buffer concentrations should be in the range of 1 to 100 mM. The immunoselective targeting agent solution may also contain a salt, such as sodium chloride or potassium chloride in a concentration of 50 to 150 mM. An effective amount of a stabilizing agent such as an albumin, a globulin, a gelatin, a protamine or a salt of protamine may also be included, and may be added to a solution containing immunotoxin or to the composition from which the solution is prepared.

Systemic administration of an immunoselective targeting agent may be made daily and is generally by intramuscular injection, although intravascular infusion is acceptable. Administration may also be intranasal or by other non-parenteral routes. Immunotoxins of the present invention may also be administered via microspheres, liposomes or other microparticulate delivery systems placed in certain tissues including blood. Topical preparations are applied daily directly to the skin or mucosa and are then preferably occluded, i.e., protected by overlaying a bandage, polyolefin film or other barrier impermeable to the topical preparation.

The blood-brain barrier limits the uptake of many therapeutic agents into the brain and spinal cord from the general circulation. Molecules which cross the blood-brain barrier use two main mechanisms: free diffusion; and facilitated transport. Because of the presence of the blood-brain barrier, attaining beneficial concentrations of a given therapeutic agent in the CNS may require the use of drug delivery strategies. Delivery of therapeutic agents to the CNS can be achieved by several methods.

One method relies on neurosurgical techniques. In the case of gravely ill patients such as accident victims or those suffering from various forms of dementia, surgical intervention is warranted despite its attendant risks. For instance, therapeutic agents can be delivered by direct physical introduction into the CNS, such as intraventricular or intrathecal injection of drugs. Intraventricular injection may be facilitated by an intraventricular catheter, for example, attached to a reservoir, such as an Ommaya reservoir. Methods of introduction may also be provided by rechargeable or biodegradable devices. Another approach is the disruption of the blood-brain barrier by substances which increase the permeability of the blood-brain barrier. Examples include intra-arterial infusion of poorly diffusible agents such as mannitol, pharmaceuticals which increase cerebrovascular permeability such as etoposide, or vasoactive agents such as leukotrienes. Neuwelt and Rappoport (1984) *Fed. Proc.* 43:214–219; Baba et al. (1991) *J. Cereb. Blood Flow Metab.* 11:638–643; and Gennuso et al. (1993) *Cancer Invest.* 11:638–643.

Further, it may be desirable to administer the pharmaceutical agents locally to the area in need of treatment; this may be achieved by, for example, local infusion during surgery, by injection, by means of a catheter, or by means of an implant, said implant being of a porous, non-porous, or gelatinous material, including membranes, such as silastic membranes, or fibers.

Agents can also be delivered by using pharmacological techniques including chemical modification or screening for an analog which will cross the blood-brain barrier. The compound may be modified to increase the hydrophobicity of the molecule, decrease net charge or molecular weight of the molecule, or modify the molecule, so that it will resemble one normally transported across the blood-brain barrier. Levin (1980) *J. Med. Chem.* 23:682–684; Pardridge (1991) in: *Peptide Drug Delivery to the Brain*; and Kostis et al. (1994) *J. Clin. Pharmacol.* 34:989–996.

Encapsulation of the agent in a hydrophobic environment such as liposomes is also effective in delivering agents to the CNS. For example WO 91/04014 describes a liposomal delivery system in which the agent is encapsulated within liposomes to which molecules have been added that are normally transported across the blood-brain barrier.

Another method of formulating the agent to pass through the blood-brain barrier is to encapsulate the agent in a cyclodextrin. Any suitable cyclodextrin which passes through the blood-brain barrier may be employed, including, but not limited to, J-cyclodextrin, K-cyclodextrin and derivatives thereof. See generally, U.S. Pat. Nos. 5,017,566, 5,002,935 and 4,983,586. Such compositions may also include a glycerol derivative as described by U.S. Pat. No. 5,153,179.

Delivery may also be obtained by conjugation of a therapeutic agent to a transportable agent to yield a new chimeric transportable therapeutic agent. For example, vasoactive intestinal peptide analog (VIPa) exerted its vasoactive effects only after conjugation to a monoclonal antibody (Mab) to the specific carrier molecule transferrin receptor, which facilitated the uptake of the VIPa-Mab conjugate through the blood-brain barrier. Pardridge (1991); and Bickel et al. (1993) *Proc. Natl. Acad. Sci. USA* 90:2618–2622. Several other specific transport systems have been identified, these include, but are not limited to, those for transferring insulin, or insulin-like growth factors I and II. Other suitable, non-specific carriers include, but are not limited to, pyridinium, fatty acids, inositol, cholesterol, and glucose derivatives.

Blood brain barrier transport compounds are known in the art and include docosohexaenoic acid, a transferrin receptor binding antibody, cationized albumin, Met-enkephalin, lipoidal forms of dihydropyridine, and cationized antibodies. See, e.g., U.S. Pat. No. 6,225,444.

Utility

The immunoselective targeting agents of the invention find use in a variety of research and therapeutic applications.

Methods of Selective Cell Killing

The high specificity and rapid action of the immunotoxin of the invention against target cells (e.g., as in the specific of the anti-VAChT-cytotoxin immunotoxin against cholinergic neuronal cells) lends itself to many applications. For example, the compositions of the invention find use in methods of selectively ablating target cells, either in vitro or in vivo.

In general, the methods of the invention relating to selective killing of target cells involves contacting a target cell in a population of cells (which population can comprise target cells and non-target cells) with an immunotoxin that specifically binds a target antigen (e.g., vesicular transporter) on the target neuronal cell. The target vesicular transporter polypeptide is surface-accessible. The immunotoxin is contacted with the target cell under conditions that allow for specific binding of the immunotoxin to the target antigen, and for killing by the cytotoxin. Generally, such is accomplished under conditions of, for example, conditions of physiological pH and osmolarity, and for a time sufficient to allow for specific binding and action of the cytotoxin (e.g., at least a few minutes (from about 1 minute to about 60 minutes, e.g., from about 1 minute to about 5 minutes, from about 5 minutes to about 15 minutes, from about 15 minutes to about 30 minutes, or from about 30 minutes to about 60 minutes) to several hours (e.g., 2 hrs, 5 hrs, 10 hrs, 12, hrs, 24 hrs, or up to 48 hrs).

Immunotoxins can be administered to a subject either singly or in a cocktail containing two or more immunotoxins. The immunotoxin can be administered with other therapeutic agents, compositions, or the like, including, but not limited to, immunosuppressive agents, tolerance-inducing agents, potentiators and side-effect relieving agents. For example, it may be desirable to administer immunosuppressive agents useful in suppressing allergic reactions of a host. Exemplary immunosuppressive agents include, but are not necessarily limited to, prednisone, prednisolone, cyclophosphamide, cyclosporine, 6-mercaptopurine, methotrexate, azathioprine and intravenous gamma globulin or their combination. Exemplary potentiators include monensin, ammonium chloride, perhexiline, verapamil, amantadine and chloroquine. All of these agents are administered in generally-accepted efficacious dose ranges such as those disclosed in the Physician's Desk Reference, 41st Ed., Publisher Edward R. Barnhart, New Jersey (1987). Administration of an immunotoxin as an immunosuppressive agent is described in, for example, WO 89/069767.

Research Applications

In one aspect, the immunotoxins of the invention find use as reagents in experimental research. For example, the anti-VAChT immunotoxin, can be used as a reagent in the study of the mechanisms underlying retinal development. As illustrated in the Examples below, the anti-VAChT immunotoxin was found useful as a reagent in the study of the On/Off neural mechanism of the developing retina by providing a reagent for selective depletion of cholinergic neurons.

The immunotoxins of the invention are also useful as reagents to examine the influence of specific cell types upon developmental processes or the role of specific cell types in various biological phenomena. For example, the selective depletion of cholinergic amacrine cells in the developing and adult retina can be used to examine whether a complete elimination of retinal interneurons influences directional selectivity or other visual response properties of retinal ganglion cells.

The immunotoxins of the invention can also be used to create animal models of diseases and disorders (such as those exemplified above), and to serve as "reagents" for the study of developmental processes. Animal models can be created in various tissues and organs of any of a variety of non-human animals. Exemplary tissues and organs in which target cells can be selectively depleted or ablated include, but are not necessarily limited to, eye (e.g., retina), brain, small intestine, reproductive tract, and the like. Of particular interest is the abalation of cholinergic neurons in these tissues or organs. Exemplary non-human animals suitable for use in production of such animal models include, but are not necessarily limited to, rodents (e.g., mice, rats, guinea pigs, and the like), rabbits, ferrets, cats, dogs, horses, cattle, reptiles (e.g., snakes, lizards, and the like); nematodes; amphibians; aplysia; etc. Other suitable animals will be readily apparent to the ordinarily skilled artisan upon reading the present specification. Likewise, models of disease can be created in culture using isolated tissues or organs from human or non-human animal sources.

Therapeutic Applications

The immunotoxins of the invention can also be used in therapeutic applications. For example, the anti-VAChT immunotoxin of the invention can be used to treat neurological disorders such as Alzheimer's disease, Parkinson's disease, and other disorders associated with (e.g., are caused by or have as a symptom) aberrant, excessive neuronal stimulation or cellular function.

Immunotoxins of the invention are also useful in treatment of human autoimmune diseases and in the treatment of diseases in which depletion of a particular cell type is a goal, such as cancer. For example, treatment of autoimmune diseases with immunotoxins is described in International Publication No. WO89/06968.

Immunotoxins of the invention can be used in addition to or in lieu of botulinum toxin (BoTox) in the treatment of conditions susceptible to BoTox treatment, e.g. treatment of wrinkle, ticks, hyperhydrosis and the like.) (see, e.g., Heckmann et al. 2001, N Engl J Med, 344(7):488–493 "Botulinum toxin A for axillary hyperhydrosis (excessive sweating); Sposito et al., Aesthetic Plast Surg. 2002 March–April; 26(2):89–98 "New indications for botulinum toxin type A in treating facial wrinkles of the mouth and neck"; Becker-Wegerich, et al. Clin Exp Dermatol. 2001 October; 26(7): 619–30. Review "Botulinum toxin A in the therapy of mimic facial lines". In these embodiments, a subject immunotoxin is administered at or near a site of wrinkles or facial tick, e.g., by injection (e.g., intradermal, subcutaneous, etc.) or by topical administration.

Gastric ulcer, depression, schizoprenia are some other conditions that can be treated with an immunotoxin according to the invention.

Methods of Promoting Cell Survival

Immunoselective targeting agents of the invention are useful in methods of promoting cell survival, e.g., reducing apoptosis.

Immunoselective agents of the invention that comprise, attached to an antibody specific for a vesicular transporter, a substance that promotes cell survival reduce apoptosis in a cell. Whether apoptosis is reduced can be assayed using any known method. Assays can be conducted on cell populations or an individual cell, and include morphological assays and biochemical assays. A non-limiting example of a method of determining the level of apoptosis in a cell population is TUNEL (TdT-mediated dUTP nick-end labeling) labeling of the 3'-OH free end of DNA fragments produced during apoptosis (Gavrieli et al. (1992) *J. Cell Biol.* 119:493). The TUNEL method consists of catalytically adding a nucleotide, which has been conjugated to a chromogen system or to a fluorescent tag, to the 3'-OH end of the 180-bp (base pair) oligomer DNA fragments in order to detect the fragments. The presence of a DNA ladder of 180-bp oligomers is indicative of apoptosis. Procedures to detect cell death based on the TUNEL method are available commercially, e.g., from Boehringer Mannheim (Cell Death Kit) and Oncor (Apoptag Plus).

Another marker that is currently available for assaying for apoptosis is annexin, sold under the trademark APO-PTEST™. This marker is used in the "Apoptosis Detection Kit," which is also commercially available, e.g., from R&D Systems. During apoptosis, a cell membrane's phospholipid asymmetry changes such that the phospholipids are exposed on the outer membrane. Annexins are a homologous group of proteins that bind phospholipids in the presence of calcium. A second reagent, propidium iodide (PI), is a DNA binding fluorochrome. When a cell population is exposed to both reagents, apoptotic cells stain positive for annexin and negative for PI, necrotic cells stain positive for both, live cells stain negative for both. Other methods of testing for apoptosis are known in the art and can be used, including, e.g., the method disclosed in U.S. Pat. No. 6,048,703.

Generally, an immunoselective targeting agent of the invention that comprises, attached to an antibody specific for a vesicular transporter, a substance that promotes cell survival reduce apoptosis in a cell, is contacted with a population of cells in vivo, which population comprises both target neuronal cells and non-target neuronal cells. The immunoselective targeting agent binds to target neuronal cells, and delivers the cell survival promoting substance to target cells.

Research Applications

Immunoselective targeting agents that comprise a cell survival promoting substance are useful in research applications, e.g., to determine the effect of a test immunoselective targeting agent on cell survival. For example, the ability of a test immunoselective targeting agent to promote cell survival in a non-human animal model of a neurodegenerative disorder is examined by administering the test agent to the animal model, and determining the effect of the agent on survival of neuronal cellss. Animal models of neurodegenerative disorders are known in the art. Animal models of Alzheimer's Disease are known in the art. See, e.g., U.S. Pat. Nos. 6,046,381; 6,175,057; and 6,172,277. Animal models of Parkinson's Disease are known in the art. See, e.g., Kim et al. (2002) *Nature* 418:50–56; and Goldberg et al. (2002)

J. Neurosci. 22:4639–4653. Animal models of Huntington's Disease are known in the art. See, e.g., Hickey et al. (2002) J. Neurochem. 81:46–59.

Therapeutic Applications

Immunoselective agents of the invention that comprise, attached to an antibody specific for a vesicular transporter, a substance that promotes cell survival are useful for treating neurological disorders that result from, are caused by, or are associated with, death of a neuronal cell or cells. Disorders amenable to treatment using a subject immunoselective agent include, but are not limited to, neurodegenerative disorders of both acute types (e.g. stroke, head trauma, Bell's palsy, spinal cord and other nerve crush injuries) and chronic types (e.g. Alzheimer's disease, Parkinson's disease, Picks's disease, amyotrophic lateral sclerosis, Huntington's disease, multiple sclerosis, myastenia gravis, glaucoma, as well as idiopathic neuropathies).

Accordingly, the invention provides methods of treating a neurological disorder that results from, is caused by, or is associated with, death of a neuronal cell. The methods generally involve administering to an individual in need thereof an amount of a subject immunoselective targeting agent that is effective to reduce apoptosis, and promote cell survival.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Construction and Purification of an Immunotoxin Targeted to Cholinergic Amacrine Cells A single-step procedure was used to conjugate the protein toxin, saporin, to the goat anti-VAChT (vesicular acetylcholine transporter) polyclonal antibody using EDC coupling chemistry (Davis and Preston, 1981 Analyt. Biochem. 116: 402–407; Nakajima and Ikada, 1995 Bioconjugate Chemistry 6:123–130). Saporin (Sigma, St. Louis, Mo.) was dissolved in conjugation buffer (0.1 M MES, 0.9 M NaCl, pH 4.7) and mixed with anti-VAChT antibody (Chemicon International, Temecula, Calif.) in equal amounts (250 μg each) and incubated at room temperature for 2 hr in the presence of EDC (Pierce, Rockford, Ill.) following the vendor's instructions. The carbodiimide (EDC) initially reacts with the carboxyl groups available on both saporin and the IgG molecule to form active, unstable O-acylurea intermediates that in turn react with primary amines to form amide bonds. The formation of covalent bonds makes the anti-VAChT-saporin conjugate highly stable. The immunotoxin was recovered following overnight dialysis against phosphate-buffered saline and stored in aliquots at −80° C. Protein concentrations were determined by microtiter plate assay on a SpectraMax 340 spectrophotometer (Molecular Devices, Sunnyvale, Calif.) at 595 nm using the Bio-Rad Protein Assay (Hercules, Calif.).

Without being held to theory, FIGS. 1A and 1B provide schematic illustrations of the structure and cellular mechanisms of action of the anti-VAChT-saporin immunotoxin. FIG. 1A shows bi-directional amide bonds produced by the EDC reaction. Six or fewer saporin molecules can bind to an individual IgG, and multi-conjugate complexes can form whose size depends on the length of the reaction. FIG. 1B shows the presumed mechanism by which the conjugated toxin kills cholinergic amacrine cells. The cholinergic cell transports ACh and VAChT to the cell surface during release of neurotransmitter (1), which exposes the VAChT antigen to anti-VAChT-saporin (2). Vesicular recycling and endosomal processing then bring the toxin into the cell and release it in the cytosol (3). The insert in FIG. 1B shows the highly specific N-glycosidase activity of RIPs, which disrupts the elongation factor II (EF-II) binding domain on the 28S ribosomal subunit.

The immunotoxin used in the Examples provided herein was produced by two hours of EDC reaction in the present of 200 μl anti-VAChT (0.862 μg/μl) with 200 μl of saporin (1.0 μg/μl). Following dialysis to remove free saporin, 400 μl of reaction product with a final concentration of 0.705 μg total protein/μl was obtained.

Example 2

Identification of Cholinergic Amacrine Cells in the Developing Rat Retina

The following methods and materials were used in the present and subsequent Examples provided herein.

Methods and Materials

Intraocular Injections: Timed-pregnant and adult Long-Evans rats were obtained from Simonsen Laboratories (Gilroy, Calif.). Rat pups were anesthetized by hypothermia and intraocular injections made using a 5 μl Hamilton syringe with a 30-gauge blunt tip needle attached to a micromanipulator. The injections were made into the temporal portion of the sclera at the level of the ora serrata. Five dilutions of the immunotoxin preparation were used, 700 ng/ml, 350 ng/ml, 70 ng/ml, 35 ng/ml and 7 ng/ml, brought to a total injection volume of 2.0 μl with sterile PBS. Control animals from the same litters were injected with vehicle (immunotoxin omitted), anti-VAChT antibody, saporin, keyhole limpet hemocyanin (KLH)-saporin and goat anti-rabbit IgG-saporin (Chemicon International).

Tissue Preparation and Immunochemistry: Animals were sacrificed by a lethal injection (i.p.) of sodium pentobarbital (0.6 mg/kg body weight) at time points ranging from 1 hr to 30 days. All but the very youngest animals (<48 hr) were transcardially perfused with ice-cold saline followed by 4% paraformaldehyde (PFA). The eyecups were removed, hemisected, and postfixed with 4% PFA for 2–4 hr, followed by immersion in 25% sucrose solution to cryoprotect the tissue before embedding in OCT compound (Tissue Tek, Torrance, Calif.). Vertical sections were cut at a thickness of 10–12 μm on a Leica 1900 cryostat (Bannockburn, Ill.) and mounted on poly-L-lysine-coated slides (Sigma).

For labeling of cholinergic cells, sections were incubated with anti-VAChT or anti-ChAT antibodies (Chemicon International). The length of the retina, the thickness of its layers, and the total number of cells in the ganglion cell layer were counted by means of DAPI DNA-labeling dye (Vector Laboratories, Burlingame, Calif.). All ganglion cells and a subset of amacrine cells in the ganglion cell layer were identified with a monoclonal antibody to parvalbumin (Sigma). On- and Off-cone bipolar cells were labeled with a rabbit polyclonal antibody to recoverin, and dopaminergic amacrine cells were labeled using a sheep polyclonal antibody to tyrosine hydroxylase (Chemicon International).

Primary antibodies were diluted in blocking solution containing normal serum, BSA and Triton X-100 overnight at 4° C. After several washes with PBS, the sections were incubated with fluorescently-labeled secondary antibodies (Vector Laboratories, or Molecular Probes, Eugene, Oreg.) diluted 1:600 in PBS-BSA for 1 hr at room temperature. For tracking of the immunotoxin after injection, sections were blocked, washed and exposed to fluorescently-labeled secondary antibodies, without application of primary antibodies. Other sections were incubated with biotinylated secondary antibodies (diluted 1:300 in PBS-BSA) for 1–2 hr at room temperature. After several washes with PBS-BSA, the sections were incubated with the HRP-containing ABC solution (Vector Laboratories) for 1–2 hr at room temperature, and then treated with a 0.5 mg/ml diaminobenzidine (DAB) solution in the presence of H2O2 for 10–30 minutes until a precipitate was formed at the site of antibody binding. Slides were cover-slipped with Vectashield mounting media (Vector Laboratories), with or without DAPI, or with glycerol.

Data Analysis: The methods using transverse retinal sections to estimate the magnitude of immuno-labeled cell populations have been previously described (White and Chalupa, 1991 *J. Comp. Neurol.* 304:1–13). Counts of labeled cells were made in a minimum of 10 sections, taken from representative microscopic fields at 40×(including peripheral, paracentral and central segments), and every immuno-positive cell was counted. Estimates were obtained of the number of cells using well-established stereological techniques as described in Gunhan-Agar et al. (2000). The immunostaining pattern and cell counts obtained from the retinal sections provide an estimate of the total number of cells in each retina, the spatial distribution of these neurons across the retinal surface, and the laminar localization of the cell types within the retinal layers. In addition, the thickness of the different retinal layers was measured to provide an index of the overall dimension of the treated and control retinas. Mean cell counts from each section were compared by the Student's t-test, with a significance level of $p<0.05$, and are expressed as overall mean±SEM.

Developmental Expression of Cholinergic Neurons in Rat Retina.

FIGS. 2A–2J show the developmental time course of cholinergic amacrine cells in the rat retina using antibodies that recognize cholinergic-specific markers, VAChT (FIGS. 2A–2E) and ChAT (FIGS. 2F–2J). VAChT immunoreactivity is evident on the day of birth, postnatal day zero (P0), shown in panel A. ChAT immunoreactivity is first detectable approximately 48 hours later (FIG. 2F). While VAChT labeling is largely confined to somas in the IPL at P0, two distinct strata of cholinergic processes become clearly evident within the IPL by P2 (FIG. 2B). Thus, in the developing retina the expression of the cholinergic phenotype occurs very early, making it feasible to target cholinergic amacrine cells by means of their vesicular transporter as early as the day of birth.

FIGS. 2A–2J show two previously-described immunochemical markers for cholinergic amacrine cells in the developing rat retina, VAChT in the column on the left and ChAT on the right. The images are vertical sections of retinas with the inner, or corneal, side at the bottom of the section. Antibody labeling is shown in red, counterstained with DAPI nuclear stain in blue. From top to bottom the images show marker expression on the day of birth (FIGS. 2A and 2F, postnatal day zero, P0), P2 (FIGS. 2B and 2G), P6 (FIGS. 2C and 2H), P12 (FIGS. 2D and 2I), and in the adult (FIGS. 2E and 2J). The layers of the immature postnatal retina (panel F) include the ventricular zone (VZ), the inner plexiform layer (IPL) and the ganglion cell layer (GCL). In the mature retina (panel J), the layers are the outer nuclear, or photoreceptor, layer (ONL), the outer plexiform layer (OPL), the inner nuclear layer (INL), the IPL and the GCL. Arrows show the earliest VAChT staining at P0 (panel A) and arrowheads show the earliest ChAT staining at P2 (panel G).

Example 3

Distribution of the Immunotoxin after Injection

Direct application of a fluorescent secondary antibody that recognizes goat-anti-VAChT was used to track the distribution of the immunotoxin following intraocular injection (FIGS. 3A–3F). The toxin was detectable in fixed retinas within one hour of the injection (data not shown). By three hours after the injection, the immunotoxin diffused across the IPL (arrowheads) into the presumptive inner nuclear layer of the ventricular zone (FIG. 3A). At this time, the immunotoxin appeared to bind to cells at the outer edge of the ganglion cell layer and the inner edge of the inner nuclear layer (arrows), reminiscent of the labeling pattern observed for the cholinergic amacrine cell population (see FIGS. 2H–I).

Six hours after injection, the concentration of the immunotoxin appeared more intense in the IPL, but the overall-labeling pattern remained largely unchanged (FIG. 3B). By 12 hours after injection, the staining intensity of the immunotoxin began to decrease, so that by 24 hrs it was virtually absent from cellular profiles (FIGS. 3C–3E). Five days after the injection (at P6), no trace of the immunotoxin could be detected in the inner layers of the retina (FIG. 3F). The small amount of staining seen in the OPL and at the outer surface of the retina is non-specific binding of the CY3-labeled secondary antibody that was also seen in vehicle-injected retinas.

In FIGS. 3A–3F, retinal cross-sections are shown with the GCL at the bottom of the frame. The red fluoresecence is produced by the direct application of Cy-3-conjugated anti-goat antibodies, with the immunotoxin itself acting as the primary antibody in the reaction. FIGS. 3A–3D are PI retinas collected 3, 6, 12 and 18 hours after toxin injection. FIG. 3E is a P2 retina (24 hr after injection) and panel F is a P6 retina (5 days after injection). Arrowheads show the toxin concentrated in the IPL and arrows show the toxin concentrated in cells immediately adjacent to the IPL.

Example 4

Elimination of Cholinergic Amacrine Cells in the Immunotoxin-Treated Retinas

The following example demonstrates that the anti-VAChT immunotoxin efficiently eliminates cholinergic amacrine cells in the developing retina. The effect of a single intraocular injection of the immunotoxin in the P1 rat was assessed at several concentrations, ranging from 700 ng/µl to 7 ng/µl.

The animals were sacrificed at 24 hrs to 30 days, and their retinas examined for the presence of cholinergic cells by ChAT labeling. FIGS. 4A–4D show a comparison of ChAT immunoreactivity (red) following treatment with the vehicle control (left column) or toxin (right column) in animals sacrificed at P2 (top row) or at P6 (bottom row). FIG. 4B shows that the immunotoxin began to disrupt the morphological integrity of cholinergic amacrine cells by P2. Note that the distribution of ChAT immunoreactivity appears similar to the secondary antibody-labeling pattern seen at P2 (FIG. 3E). FIG. 4D shows that at P6, five days after injection, treatment with the toxin resulted in complete elimination of CHAT immunoreactivity, coincident with the loss of detectable immunotoxin seen in FIG. 3F. Retinas were examined up to a month after treatment without detecting the presence of any cholinergic amacrine cells (data not shown).

Retinal cross-sections from rats injected at P1 in FIGS. 4A–D are shown with the GCL at the bottom, immunostained for ChAT (red) against a background of DAPI nuclear stain (blue). FIGS. 4A and 4B are retinas from rats sacrificed at P2 and FIGS. 4C and 4D are retinas from rats sacrificed at P6. Arrows show perceptible changes in ChAT immunoreactivity at P2, while arrowheads show complete loss of cholinergic amacrine cells by P6.

Example 5

Target Cell Specificity of the Anti-VAChT Immunotoxin

Several control injections were used to confirm the specificity of the immunotoxin in causing amacrine cell loss. FIG. 5A shows a comparison of the number of cholinergic amacrine cells labeled with ChAT (per mm$^3$) in animals injected with the vehicle, unconjugated anti-VAChT antibody, free saporin, saporin conjugated to either a non-specific antibody (goat anti-rabbit IgG) or a non-IgG protein (KLH, keyhole limpet hemocyanin), and dilutions of the immunotoxin up to 100-fold. Neither vehicle nor unconjugated anti-VAChT antibody affected cholinergic amacrine cell number. Free saporin, however, reduced the number of cells by approximately 30% of untreated controls ($p<0.001$), which suggests that unconjugated saporin is capable of entering neurons, and that incomplete dialysis could cause non-specific cell death. Saporin conjugated to either a non-specific antibodies (goat anti-rabbit IgG) or non-IgG protein (KLH, keyhole limpet hemocyanin) did not affect cholinergic amacrine cell number. These control data demonstrate collectively that the loss of cholinergic amacrine cells observed in the immunotoxin-treated retinas is specific to the immunotoxin.

At concentrations of 700 ng/μl to 35 ng/μl the immunotoxin eliminated essentially all of the cholinergic amacrine cells in the retina. At the lowest concentration (7 ng/μl) a small number of cholinergic amacrine cells were detected in the retinal periphery. At higher dosages (700 ng/μl to 350 ng/μl) there was an indication of a general disruption of retinal structure, as evidenced by decreases in the length and thickness of retinas, and in the organization of the inner layers. Thus, in subsequent cases we used dosages within the optimal range (35 ng/μl to 70 ng/μl) to attain complete elimination of cholinergic amacrine cells.

Vehicle-treated control retinas, as well as retinas injected with the effective doses described above, showed a decrease in the overall size of the eyecup. In sections containing the optic nerve head for comparison, the linear diameter of the retina decreased approximately 14% from untreated controls after injection of either vehicle or the immunotoxin (both $p<0.001$), but the two injected groups did not differ from each other. Injection of vehicle also reduced the thickness relative to normal of the ONL (~9%, $p=0.011$), the OPL (~24%, $p<0.001$) and the IPL (~8%, $p=0.015$), but not the INL or the GCL. Toxin treatment reduced the thickness relative to normal of the ONL (~12%, $p=0.006$), the OPL (~6%, $p<0.001$), the IPL (~14%, $p=0.001$) and the GCL (~12%, $p=0.014$), but not the INL. Only the thickness of the IPL was different between vehicle- and immunotoxin-treated retinas. The immunotoxin decreased the thickness of this synaptic layer by approximately 6% ($p=0.018$).

To determine the specificity of the immunotoxin effects, counts were made of different cell types that either synapse directly with, or are in close proximity to, cholinergic amacrine cells from vehicle-injected and toxin (70 ng/μl)-injected retinas. The counts included: (i) the total number of nuclei in the GCL (labeled by DAPI for nuclear staining); (ii) parvalbumin-positive cells in the ganglion cell layer, which includes ganglion cells and a small subset of AII amacrine cells (Uesugi et al., 1992 *Exp. Eye Res.* 54(4): 491–499; Wassle et al., 1993 *J. Comp. Neurol.* 332(4): 407–420); (iii) recoverin-positive cone bipolar cells (Milam et al., 1993; Euler and Wassle, 1995 *J. Comp. Neurol.* 361:461–478); and (iv) tyrosine hydroxylase-positive dopaminergic amacrine cells (Kolb et al., 1991 *J. Comp. Neurol.* 310:267–284; Dacey, 1990 *J. Comp. Neurol.* 301: 461–489). Values are again mean±SEM. These cell populations did not differ significantly in vehicle-treated and toxin-treated retinas, suggesting that the immunotoxin acts selectively to eliminate cholinergic amacrine cells (See FIG. 5B).

Example 6

Effect of Anti-VAChT Immunotoxin Upon Bipolar Axonal in-Growth

The effect of the anti-VAChT immunotoxin upon bipolar cell axonal in-growth was then examined. The early depletion of ganglion cells does not disrupt the formation of stratified On and Off cone bipolar cell pathways (Gunhan-Agar et al., 2000 *J. Neuroscience* 20:306–314). The other major synaptic target of On and Off cone bipolar cells are cholinergic amacrine cells whose processes form two distinct strata within the IPL (see FIGS. 2A–2J) more than a week before the ingrowth of cone bipolar cell axons. These observations led to the hypothesis that cholinergic processes provide a "scaffold" for the subsequent segregation of On and Off cone bipolar cells. The availability of the immunotoxin of the present invention provided an opportunity to test the merits of this hypothesis.

FIGS. 6A–6D depict P1-injected rat retinas double-labeled with recoverin for cone bipolar cells (green) and VAChT for cholinergic amacrine cells (red) at a series of different time points, including P2, P6, P12 and P20 (FIGS. 6A–6D, respectively). The top panels in each figure are vehicle-injected while the lower images are toxin-injected retinas. Note the similarities between the VAChT staining in the top series of panels and those in FIGS. 2A–2J. Note also that in the complete absence of VAChT immunoreactivity cone bipolar cells migrate from the ventricular zone, extend their axons into the IPL, and form two distinct On and Off strata within this synaptic layer.

Also these cells precede the migration of cone bipolar cells from their birthplace near the top of the VZ (FIG. 6B). Even in the complete absence of VAChT immunoreactivity, cone bipolar cell somas migrate from the ventricular zone (arrows, FIGS. 6C and 6D) and extend their axons to two distinct strata in the IPL, much as do cells in vehicle-treated retinas (arrowheads, FIGS. 6C and 6D).

Example 7

Axonal Targeting of Bipolar Cells is Tightly Controlled

FIGS. 7A–7B provide a P12 retina double labeled with anti-recoverin for cone bipolar cells (green) and anti-VAChT for cholinergic amacrine cells (red). The top panels in each of FIGS. 7A–7B are vehicle-injected and the bottom panels are toxin-injected retinas. The two low magnification panels of FIG. 7A show that the general morphology of the retina, particularly that of the cone bipolar cells, is unaffected by immunotoxin treatment.

The higher magnification images of FIG. 7B show that fine cone bipolar cell structures and axonal targeting are also largely unaffected by the loss of cholinergic amacrine cells. In the top panel of FIG. 7B, note that On cone bipolar cells terminate on the outer side of the amacrine layer (arrows); while Off cone bipolar cells terminate on the inner side of the amacrine layer (arrowheads). It is striking that even in the complete absence of their amacrine cell targets, the axon terminals of On and Off cone bipolar cells attain a stratified state, indistinguishable from that found in the normal retina.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An immunotoxin comprising a cytotoxin conjugated to an antibody that specifically binds a cell surface-accessible epitope of a vesicular transporter protein on the surface of a neuronal cell, which transporter protein is transiently cell surface accessible, wherein the immunotoxin, when contacted with a neuronal cell displaying the transporter protein on its surface, kills the neuronal cell.

2. The immunotoxin of claim 1, wherein the cytotoxin is a ribosome-inactivating protein (RIP).

3. The immunotoxin of claim 2, wherein the RIP is selected from the group consisting of a Type I RIP and a Type II RIP.

4. The immunotoxin of claim 2, wherein the RIP is selected from the group consisting of saporin, luffin, momordins, ricin, and abrin.

5. The immunotoxin of claim 2, wherein the RIP is saporin.

6. The immunotoxin of claim 1, wherein the vesicular transporter protein is selected from the group consisting of a monoamine transporter, an acetylcholine transporter, a gamma-aminobutyric acid transporter, and a glutamate transporter.

7. The immunotoxin of claim 1, wherein the neuronal cell is a cholinergic cell.

8. The immunotoxin of claim 1, wherein the transporter protein is a vesicular acetylcholine transporter (VAChT).

9. The immunotoxin of claim 8, wherein the antibody is an anti-VAChT monoclonal antibody.

10. The immunotoxin of claim 1, wherein the cytotoxin molecule and antibody are covalently attached by reaction with 1-ethyl-3[3-dimethylaminopropyl] carbodiimide hydrochloride.

11. The immunotoxin of claim 1, wherein the immunotoxin comprises at least 2 cytotoxin molecules per antibody molecule.

12. The immunotoxin of claim 1, further comprising a detectable label.

* * * * *